United States Patent
Koike et al.

(10) Patent No.: US 9,624,133 B2
(45) Date of Patent: Apr. 18, 2017

(54) SOLID ELECTROLYTE, METHOD OF PRODUCING THE SOLID ELECTROLYTE, AND GAS SENSOR EQUIPPED WITH GAS SENSOR ELEMENT USING THE SOLID ELECTROLYTE

(75) Inventors: Kazuhiko Koike, Okazaki (JP); Kiyomi Kobayashi, Kuwana (JP)

(73) Assignees: DENSO CORPORATION, Kariya (JP); NIPPON SOKEN, INC., Nishio (JP)

(*) Notice: Subject to any disclaimer, the term of this patent is extended or adjusted under 35 U.S.C. 154(b) by 675 days.

(21) Appl. No.: 12/700,089

(22) Filed: Feb. 4, 2010

(65) Prior Publication Data
US 2010/0200427 A1 Aug. 12, 2010

(30) Foreign Application Priority Data

Feb. 6, 2009 (JP) ................................. 2009-025474
Dec. 10, 2009 (JP) ................................. 2009-280112

(51) Int. Cl.
C04B 35/488 (2006.01)
G01N 27/407 (2006.01)

(52) U.S. Cl.
CPC ..... C04B 35/4885 (2013.01); G01N 27/4075 (2013.01); C04B 2235/3225 (2013.01); C04B 2235/6025 (2013.01); C04B 2235/656 (2013.01); C04B 2235/77 (2013.01); C04B 2235/785 (2013.01); C04B 2235/786 (2013.01); C04B 2235/85 (2013.01); C04B 2235/96 (2013.01); C04B 2235/9607 (2013.01)

(58) Field of Classification Search
CPC .......... C04B 35/4885; C04B 2235/785; C04B 2235/656; C04B 2235/85; C04B 2235/96; C04B 2235/9607
USPC .................... 205/784.5, 775, 783.5; 264/618
See application file for complete search history.

(56) References Cited

U.S. PATENT DOCUMENTS

| | | | |
|---|---|---|---|
| 5,728,636 A | 3/1998 | Nawa et al. | |
| 7,041,207 B2 * | 5/2006 | Noda et al. | ................... 204/426 |
| 7,618,731 B2 * | 11/2009 | Kumar | ................... B82Y 30/00 429/535 |
| 2007/0017806 A1 * | 1/2007 | Furuta et al. | ................. 204/424 |

FOREIGN PATENT DOCUMENTS

| | | |
|---|---|---|
| JP | 08-015213 | 1/1996 |
| JP | 2703207 | 10/1997 |
| JP | 11-310456 | 11/1999 |

* cited by examiner

Primary Examiner — Louis Rufo
(74) Attorney, Agent, or Firm — Nixon & Vanderhye P.C.

(57) ABSTRACT

A solid electrolyte is made of zirconia grains containing yttria and alumina grains dispersed in the zirconia grains. In the solid electrolyte, the yttria content per zirconia content is within a range of 2 to 10 mol. %, the relative density is not less than 93%, and the average particle size Rz of the zirconia grains is not more than 2 μm, an average particle size Ra of the alumina grains is not more than 1 μm. The average particle size Ra of the alumina grains is smaller than the average particle size Rz of the zirconia grains. An average distance value $A_{La}$ between the alumina grains is not more than 2 μm, and a standard deviation $S_{La}$ thereof is not more than 0.8. The solid electrolyte satisfies a relationship of $(S_{La}/A_{La}) \times Rz \leq 0.9$.

8 Claims, 9 Drawing Sheets

SOLID ELECTROLYTE, METHOD OF PRODUCING THE SOLID ELECTROLYTE, AND GAS SENSOR EQUIPPED WITH GAS SENSOR ELEMENT USING THE SOLID ELECTROLYTE

CROSS-REFERENCE TO RELATED APPLICATION

This application is related to and claims priority from Japanese Patent Applications No. 2009-25474 filed on Feb. 6, 2009, and No. 2009-280112 filed on Dec. 10, 2009, the contents of which are hereby incorporated by reference.

BACKGROUND OF THE INVENTION

1. Field of the Invention

The present invention relates to a solid electrolyte for use in a gas sensor element in a gas sensor, which is capable of detecting a concentration of a specific gas component contained in an exhaust gas emitted from an internal combustion engine such as diesel engines. The present invention further relates to a method of producing the solid electrolyte, and to a gas sensor equipped with a gas sensor element using the solid electrolyte.

2. Description of the Related Art

A gas sensor equipped with an exhaust gas sensor element such as a $O_2$ gas sensor element, a NOx sensor element, and an A/F (air/fuel) sensor element is used to detect a concentration of $O_2$ gas and a concentration of NOx gas contained in, and an A/F ratio of an exhaust gas emitted from an internal combustion engine such as diesel engines and gasoline engines mounted on vehicles. Each of those exhaust gas sensor elements use a solid electrolyte made of zirconia (or zirconium), for example.

In general, various types of stress are applied to the gas sensor element placed in an exhaust gas passage in an exhaust gas system connected to an internal combustion engine. For example, rapid activation of the gas sensor element causes a rapid temperature rise of the gas sensor element, and a thermal stress is given to the gas sensor element. Contacting with moisture or drop of water contained in an exhaust gas or ambient air generates stress in the inside of the gas sensor element. Still further, a rapid temperature change of the exhaust gas or a rapid change of the exhaust gas flow also generates stress in the inside of the gas sensor element.

When stress such an excess stress of not less than a predetermined allowable value is applied to the gas sensor element, a solid electrolyte in the gas sensor element breaks. The malfunction of the solid electrolyte in the gas sensor element cannot correctly detect a concentration of $O_2$ gas and a concentration of NOx gas contained in, and an A/F ratio of the exhaust gas. This decreases the reliability of the gas sensor element.

When the gas sensor element is placed under a condition at a low temperature within a range of 200 to 300° C., zirconia (or zirconium) forming the solid electrolyte transforms in phase from T phase (tetragonal phase) to M phase (monoclinic phase). In that phase transition, zirconia slightly expands in volume by approximately 4%. Expanding the volume of the gas sensor element often generates cracks in the inside of the gas sensor element. Thus, the conventional gas sensor element has such a low-temperature problem.

In addition, there is a possibility for an A/F sensor to receive a thermal shock generated by the presence of water drops contained in the exhaust gas immediately after the engine starts. However, a conventional A/F sensors do not have an adequate thermal shock resistance. In order to avoid the conventional problems of the gas sensor element described above, conventional techniques, for example, Japanese patent laid open publication No. JP H08-15213 delays the activation of an A/F sensor in order to avoid thermal shock.

Further, Japanese patent publication No. JP 2703207 discloses a technique to produce zirconia composite sintered ceramics having high mechanical strength and fracture toughness by using nano-composite material. Such nano-composite material is obtained by diffusing nano-alumina into zirconia and partially stabilized zirconia (which uses ceria and titania (or titanium dioxide) as stabilizing agent).

Still further, the technique disclosed in Japanese patent laid open publication No. JP H11-310456 shows solid electrolyte composite sintered ceramics having high mechanical strength and fracture toughness, and high ion conductivity by using nano-composite material capable of dispersing ceramic grains such as SiC, AlN, BN, $ZrB_2$, and $Si_3N_4$ into stabilized zirconia grains (which use yttria as stabilizing agent).

On the other hand, in order to avoid thermal shock, conventional techniques such as Japanese patent laid open publication No. JP H08-15213 disclose delaying the activation of the A/F sensor. However, this conventional technique decreases the efficiency of purifying the exhaust gas during the period of avoiding thermal shock because it is difficult to perform the A/F control during the period of avoiding thermal shock.

Further, because another conventional technique disclosed in Japanese patent publication No. JP 2703207 disperses alumina grains into zirconia grains, this increases electric resistance of the zirconia grains. Therefore it is difficult for that technique to adequately obtain the ion conductivity of the zirconia composite sintered ceramics.

Still further, like the technique disclosed in the Japanese patent publication No. JP 2703207 described above, because the technique disclosed in the Japanese patent laid open publication No. JP H11-310456 disperses alumina grains in zirconia grains, this technique also increases the electric resistance of the zirconia grains, and cannot adequately keep the ion conductivity of the solid electrolyte composite sintered ceramics. Further, because those grains are sintered or fired in non-oxidative atmosphere, oxygen contained in alumina grains in contact with a mixture of non-oxide and zirconia grains is lost, and this decreases the mechanical strength of the solid electrolyte composite sintered ceramics. It is therefore difficult for the solid electrolyte composite sintered ceramics to have adequate thermal shock resistance.

SUMMARY OF THE INVENTION

It is an object of the present invention to provide a solid electrolyte having high ion conductivity and thermal shock resistance capable of suppressing a low-temperature deterioration, a method of producing the solid electrolyte, and a gas sensor composed of a gas sensor element using the solid electrolyte.

To achieve the above purposes, the present invention provides a solid electrolyte for use in a gas sensor element. The solid electrolyte according to a first aspect of the present invention is composed of zirconia grains and alumina grains in which the zirconia grains use yttria which serves as stabilizing agent, and the alumina grains are dispersed in at least the grain boundaries of the zirconia grains. In particular, the solid electrolyte is made of a yttria content within a range of 2 to 10 mol. % per zirconia content, the alumina content of the entire solid electrolyte is within a range of 5 to 25 mass %, and the relative density of the zirconia to the alumina is not less than 93%. The zirconia grains have an average particle size Rz or diameter is not more than 2 μm, the alumina grains have an average particle size Ra of not more than 1 μm, and the average particle size Ra of the alumina grains is smaller than the average particle size Rz of the zirconia grains. The average distance value $A_{La}$ between the alumina grains is not more than 2 μm, and a standard deviation $S_{La}$ of the average distance value $A_{La}$ between the alumina grains is not more than 0.8. The average particle size Rz of the zirconia grains, the average distance value $A_{La}$ between the adjacent alumina grains, and the standard deviation $S_{La}$ satisfy a relationship of $(S_{La}/A_{La}) \times Rz \leq 0.9$.

In accordance with a second aspect of the present invention, there is provided a method of producing the solid electrolyte for use in a gas sensor element. The method is comprised of: (a) a first pulverizing step of adding yttria into zirconia, dry-mixing them, pulverizing them to make a zirconia mixed powder; (b) a second pulverizing step of adding a solvent into the zirconia mixed powder, and pulverizing the zirconia mixed powder of a large particle size; (c) a first mixing step of adding alumina slurry containing alumina grains having an average particle size of not more than 0.5 μm into the zirconia mixed powder, and mixing them to make an intermediate mixture; (d) a second mixture step of mixing binder and plasticizer into the intermediate mixture to make a slurry; (e) a step of shaping or molding the slurry into a sheet shape to make a zirconia sheet; and (f) a step of firing the zirconia sheet to make the solid electrolyte for use in a gas sensor element.

In accordance with a second aspect of the present invention, there is provided a gas sensor composed of a gas sensor element, a housing, and an element cover. The gas sensor element is inserted into the inside of the housing and then placed therein. The element cover covers a front part of the gas sensor element. The gas sensor element has a sensor substrate having a pair of electrodes formed on both surfaces of the solid electrolyte. This solid electrolyte is the solid electrolyte in accordance with the first aspect of the present invention previously described.

The solid electrolyte for use in a gas sensor (hereinafter, referred to as the "solid electrolyte" for brevity) according to the first aspect of the present invention contains the zirconia grains of a high relative density of not less than 93%, where the alumina grains are dispersed in at least the grain boundaries of the zirconia grains containing yttrium as a stabilizing agent of a specific content. Further, the solid electrolyte according to the present invention satisfies the specific dispersion state of dispersing the alumina grains into the grain boundaries of the zirconia grains which have the specific average particle size Rz so that the alumina grains having the specific average grain size Ra has the specific distance (having the average distance value $A_{La}$ and the standard deviation $S_{La}$) between the alumina grains. This structure allows the zirconia grains to have a relatively small and same particle size, and a high density.

A resistance of the solid electrolyte is a sum of an internal resistance of the zirconia grains and a resistance of the grain boundaries of the zirconia grains. In general, mixing insulation material such as alumina into zirconia increases the resistance value of the zirconia.

On the other hand, as described above, although the internal resistance of the zirconia grains is generally increased by dispersing alumina grains into the zirconia grains, the present invention disperses the alumina grains into the zirconia grains under the specific condition, and this forms the grain boundaries between the zirconia grains with a high density, and the grain boundaries thereby strongly contact with each other, or are strongly adhered together. Therefore current can easily flow into the zirconia grains in the solid electrolyte according to the present invention. This decreases the resistance of the grain boundaries, and allows the total resistance value of the solid electrolyte, which is the sum of the internal resistance of the zirconia grains and the resistance of the grain boundaries of the zirconia grains, which becomes equal to or less than that of a case of not mixing any insulation material. Therefore the present invention can provide the solid electrolyte having a superior ion conductivity.

Even if a phase transition (which will be explained later in detail) occurs in the zirconia grains, it is possible to suppress decreasing the density of the grain boundaries and increasing the resistance of the grain boundaries because the zirconia grains has a small grain size, and this can avoid occurring a fine crack in the solid electrolyte.

The more the grain size of zirconia decreases, the more the strength of the solid electrolyte increases. The solid electrolyte according to the present invention contains the zirconia grains of a small particle size and the alumina grains having a fine particle size dispersed into at least the grain boundaries of the zirconia grains. This can suppress growing the zirconia grains, and thereby decreases the particle size of the zirconia grains. In addition, as previously described, the alumina grains of a fine particle size are dispersed into at least the grain boundaries of the zirconia grains under the specific condition, it is possible to reinforce the grain boundaries between the zirconia grains in the solid electrolyte according to the present invention. This structure increases the mechanical strength of the solid electrolyte. Therefore the solid electrolyte according to the present invention has high thermal shock resistance. It is possible to avoid generating cracks in the solid electrolyte even if stress such as thermal shock is applied to a gas sensor using the solid electrolyte according to the present invention.

In addition, because the alumina grains are dispersed into the grain boundaries of the zirconia grains, the solid electrolyte according to the present invention has an increased density of the grain boundaries between the zirconia grains, and the grain boundaries of the zirconia grains is reinforced. It is therefore difficult to generate cracks in the solid electrolyte even if a hydrothermal treatment is performed and a phase transition occurs in the zirconia grains during the production. In addition, because the zirconia grains have a small particle size, the presence of the alumina grains dispersed in the grain boundaries of the zirconia grains can suppress a phase transition of the zirconia grains even if the solid electrolyte is placed under a condition to easily cause the phase transition of the zirconia grains. Therefore even if the solid electrolyte is placed or kept under a state at a low temperature, no crack occurs in the solid electrolyte, and this avoid deterioration of the density of the grain boundaries of the zirconia grains. Thus, the structure of the solid electrolyte according to the present invention can suppress the low-temperature deterioration.

The solid electrolyte according to the present invention satisfies the relationship $(S_{La}/A_{La}) \times Rz \leq 0.9$, . . . (1), where Rz is an average particle size of zirconia grains, $A_{La}$ is an average distance value between adjacent alumina grains, and $S_{La}$ is a standard deviation of the average distance value $A_{La}$ of the alumina grains. Satisfying the relationship (1) can decrease the average particle size Rz of the zirconia grains, and provides a good dispersion of the alumina grains into the grain boundaries of the zirconia grains. Therefore this allows the solid electrolyte to have high ion conductivity and high thermal shock resistance, and suppresses the low-temperature deterioration.

As described above, the present invention provides the solid electrolyte, to be used in a gas sensor, with high ion conductivity, high thermal shock resistance, and capable of suppressing the low-temperature deterioration. It is thereby possible to provide a gas sensor element using the solid electrolyte with superior reliability.

According to the second aspect of the present invention, because the method mixes alumina slurry containing alumina grains having a predetermined particle size into zirconia grains and fires the mixture, the alumina grains of a fine particle size can be dispersed into at least the grain boundaries of the zirconia grains. This structure can suppress growing the zirconia grains during the firing step in the production, and obtain the zirconia grains having a fine and uniform particle size. This provides the solid electrolyte having the grain boundaries of the zirconia grains with a high density.

It is thereby possible to obtain the solid electrolyte for use in a gas sensor, in which the alumina grains having a fine particle size are dispersed into at least the grain boundaries of the zirconia grains. The zirconia grains contain or use yttria as stabilizing agent. This solid electrolyte, to be used in a gas sensor, has high ion conductivity and high thermal shock resistance, and suppresses the low-temperature deterioration.

According to the present invention described above, it is possible to produce the solid electrolyte for use in a gas sensor with high ion conductivity and high thermal shock resistance, and capable of suppressing the low-temperature deterioration.

The present invention in accordance with the third aspect of the present invention provides a gas sensor having a gas sensor element composed of the solid electrolyte which has high ion conductivity and high thermal shock resistance, and capable of suppressing the low-temperature deterioration. That is, even if various types of stress such as thermal shock are applied to the gas sensor element, it is possible to avoid generating cracks in the solid electrolyte, and suppress the low-temperature deterioration. Thereby it is possible for the gas sensor equipped with the solid electrolyte to correctly detect, for a long period of time, a concentration of oxygen gas and a concentration of NOx gas in an exhaust gas, and an A/F ratio of the exhaust gas. This can increase the reliability of the gas sensor.

The third aspect of the present invention equips the gas sensor with the gas sensor element having the solid electrolyte as the first aspect of the present invention. This is one of the important features of the present invention. It is therefore possible to apply the concept of the present invention to conventionally known and used gas sensors having various structures.

BRIEF DESCRIPTION OF THE DRAWINGS

A preferred, non-limiting embodiment of the present invention will be described by way of example with reference to the accompanying drawings, in which.

DETAILED DESCRIPTION OF THE PREFERRED EMBODIMENTS

Figure 1:
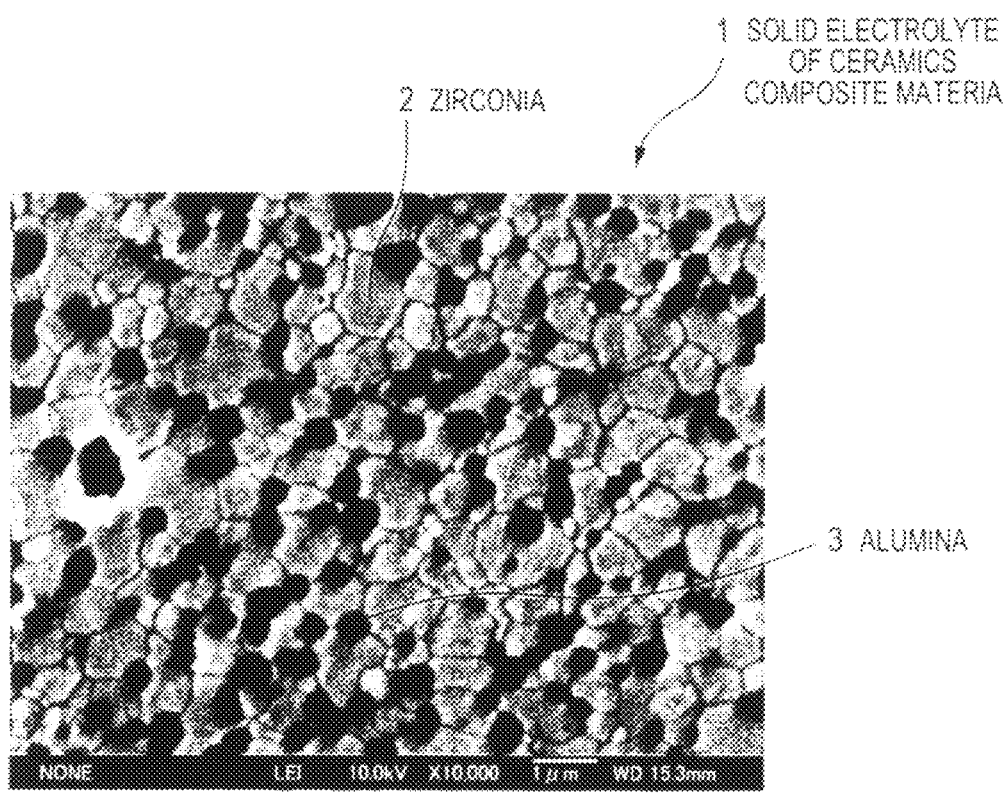
FIG. 1 is a SEM photograph of a sample E7 as a solid electrolyte according to a first embodiment of the present invention.

Hereinafter, various embodiments of the present invention will be described with reference to the accompanying drawings. In the following description of the various embodiments, like reference characters or numerals designate like or equivalent component parts throughout the several diagrams.

Preferred Embodiment of the Present Invention

Various types of gas sensors can be equipped with a gas sensor element using the solid electrolyte according to the first aspect of the present invention. In the solid electrolyte, alumina grains of a fine particle size are dispersed into at least the grain boundaries of the zirconia grains which use yttrium as stabilizing agent (or stabilizer). The zirconia grains are made of at least one of crystal phases such as a M phase (monoclinic phase), a T phase (tetragonal phase), and a C phase (cubic phase).

When the solid electrolyte is made so that no alumina grain is dispersed into the grain boundaries of the zirconia grains, the zirconia grains have lack of uniform, and gaps are formed in the grain boundaries between the zirconia grains. This decreases the mechanical strength of the solid electrolyte, and increases the electric resistance of the grain boundaries although the internal resistance of the zirconia grains is decreased because no alumina grain is dispersed in the zirconia grains.

In addition, a phase transition from T phase to M phase in the zirconia grains of the solid electrolyte causes a volume expansion of approximately 4% in the solid electrolyte. Such a phase transition of the zirconia grains generates fine cracks in the grain boundaries of the zirconia grains and thereby deteriorates the solid electrolyte. It is also acceptable to place the alumina grains in the zirconia grains in addition to the grain boundaries of the zirconia grains.

Further, because the solid electrolyte for use in a gas sensor according to the present invention and the alumina grains are simultaneously fired, it is preferable for the solid electrolyte to have the thermal expansion coefficient close to that of the alumina grains. So, it is preferable for the solid electrolyte to have the thermal expansion coefficient approximately within a range of $7.9 \times 10^{-6}/°$ C. to $9.9 \times 10^{-6}/°$ C. which is approximately ±1 time of the thermal expansion coefficient of the alumina grains.

Still further, because the alumina grains, which are dispersed, are smaller in thermal expansion coefficient than the zirconia grains, the thermal expansion coefficient of the solid electrolyte is decreased according to increasing the content of the alumina grains. Therefore it is preferable to adjust the thermal expansion coefficient of the solid electrolyte by adjusting the content of the alumina grains to be added.

The zirconia grains have an average particle size of not more than 2 μm. When the average particle size of the zirconia grains exceeds 2 μm, a gap is easily generated between the grain boundaries of the zirconia grains. This decreases the mechanical strength of the solid electrolyte, and further decreases the ion conductivity of the solid electrolyte because the resistance of the grain boundaries increases. Still further, because the alumina grains cannot suppress generating the phase transition of the zirconia grains having a large particle size, it becomes difficult to suppress the low temperature deterioration of the solid electrolyte when it is placed under a state at a low temperature. It is preferable for the particle size of the zirconia grains to have the standard deviation of not more than 1.0.

The average particle size Rz of the zirconia grains in the solid electrolyte according to the present invention are measured based on a SEM (scanning electron microscope) photograph. Specifically, a sample of the solid electrolyte is polished, and then treated by thermal etching in order to easily observe the grain boundaries of the zirconia grains. This thermal etching is performed for 20 minutes at a temperature which is below by 200° C. the sample firing temperature. A carbon film is deposited on the surface of the sample in order to observe the surface of the sample with a SEM. In the observation of the SEM photograph, the grain boundaries of all zirconia grains, which are present in a secondary electron image of the obtained SEM photograph of 10,000 magnification, are detected. Then, the grain boundaries are traced by image processing software. A diameter of each grain corresponding to a circular shape on the SEM photograph is measured and calculated. The observation and calculations are performed on three microscope fields, and an average value of the obtained diameters is calculated. The magnification of the SEM photograph is changed according to a demand of observation.

The alumina grains in the solid electrolyte has the average particle size of not more than 1 μm. When the average particle size of the alumina grains exceeds 1 μm, this decreases the effect to suppress growing the zirconia grains obtained by the presence of the alumina grains, and as a result, the zirconia grains have a large particle size and are uneven or irregular. Because this generates a gap in the grain boundaries of the zirconia grains, there is a probability to decrease the mechanical strength of the solid electrolyte, and increase the resistance at the grain boundaries, and occur a low-temperature deterioration in the solid electrolyte is likely to occur.

It is preferable for the alumina grains to have an average particle size (or average diameter) within a range of 0.4 to 0.6 μm. This structure can improve the characteristics of the solid electrolyte according to the present invention as previously described.

Further, it is preferable for the particle size of the alumina grains to have a standard deviation of not more than 0.6.

In the solid electrolyte according to the present invention, the average particle size Ra of the alumina grains is smaller than the average particle size Rz of the zirconia grains.

When the average particle size Ra of the alumina grains is larger than the average particle size Rz of the zirconia grains, stress is centered into a part of the solid electrolyte, and this has a probability to generate defects in the solid electrolyte.

The average particle size of the alumina grains in the solid electrolyte are detected by observing the SEM photograph. Specifically, a sample as the solid electrolyte is polished, and thermal etching is performed in order to observe the grain boundaries of the zirconia grains in the sample. This thermal etching is performed for 20 minutes at a temperature which is below a sample firing temperature by 200° C. A carbon film is deposited on the surface of the sample to perform the observation. Because black parts correspond to alumina grains in the SEM photograph of 10,000 magnification, binarization of the SEM photograph is performed by using image processing software in order to select the black parts. After completion of the binarization, a diameter of each grain corresponding to a circular shape is detected on binarized image data of the SEM photograph, and an average value of them is then calculated. It is possible to change the magnification of the SEM photograph according to demands.

The solid electrolyte according to the present invention has an average distance value $A_{La}$ of not more than 2 μm, and a standard deviation $S_L$ of not more than 0.8, where $A_{La}$ is the average distance value between the aluminum grains, and $S_L$ is the standard deviation of the average distance values $A_{La}$.

When the average distance value $A_{La}$ of the grain distance between the aluminum grains exceeds 2 μm, it becomes difficult to suppress growing of the zirconia grains, so that the particle size of the zirconia grain becomes large and uneven or unbalanced, that is, the particle size of them are not uniform. Because this generates a gap between adjacent zirconia grains, mechanical strength of the solid electrolyte is decreased, and a resistance of the grain boundary resistance is increased.

Further, when the standard deviation $S_{La}$ of the average distance values $A_{La}$ exceeds 0.8, the aluminum grains are not dispersed uniformly in the zirconia grains, and the distribution in particle size of the zirconia grains does not become uniform. This has a probability to decrease the mechanical strength of the solid electrolyte.

It is more preferable for the alumina grains in the solid electrolyte to have the average distance value $A_{La}$ of not more than 1.5 μm, and the standard deviation $S_{La}$ within a range of 0.5 to 0.6. This condition better disperses alumina grains into the grain boundaries of the zirconia grains in the solid electrolyte, and provides excellent characteristics such as an excellent grain boundary resistance as more decreased value.

The grain distance between adjacent alumina grains is detected by observing the SEM photographs. Specifically, a sample as the solid electrolyte is polished, and thermal etching is performed in order to observe the grain boundaries of the zirconia grains in the sample. This thermal etching is performed for 20 minutes at a temperature which is below a sample firing temperature by 200° C. A carbon film is deposited on the surface of the sample to perform the observation. Because black parts in the SEM photograph at 10,000 times magnification correspond to the alumina grains, the distance between the central points of the adjacent black grains is obtained by using image processing software. The grain distance of all of the black grains are detected and an average of them and a standard deviation of them are calculated. Those processes are performed on three microscope fields, and an average and a standard deviation of them are calculated. It is possible to change the magnification of the SEM photograph according to demands.

In the solid electrolyte according to the present invention, the average particle size Rz of the zirconia grains and the average distance value $A_{La}$ between the alumina grains, and the standard deviation $S_{La}$ have a relationship of $(S_{La}/A_{La}) \times Rz \leq 0.9$.

When $(S_{La}/A_{La}) \times Rz > 0.9$, the average particle size of the zirconia grains becomes large, and this has a probability to decrease the dispersibility of the alumina grains in the grain boundaries of the zirconia grains.

In the solid electrolyte according to the present invention, yttria content to zirconia content is within a range of 2 to 10 mol. %.

When the above yttria content is less than 2 mol. %, there is a probability to generate cracks in the solid electrolyte by a volume change of the solid electrolyte when zirconia grains transform in phase from T phase (tetragonal) to M phase (monoclinic).

On the other hand, when the above yttria content exceeds 10 mol. %, the crystal phase of the zirconia grains becomes C phase (cubic) in which the zirconia grains easily grow. Therefore even if alumina is added into the zirconia grains, the zirconia grains grow, and this has a probability to decrease the mechanical strength of the solid electrolyte.

In the solid electrolyte according to the present invention, the alumina content of the entire solid electrolyte is within a range of 5 to 25 mass %.

When the alumina content of the entire solid electrolyte is less than 5 mass %, because it is difficult to suppress growing the zirconia grains, the particle size of the zirconia grains becomes large, and the zirconia grains do not become uniformly dispersed in the solid electrolyte, the alumina grains are not dispersed uniformly in the zirconia grains, and a gap is thereby generated between the grain boundaries of the zirconia grains.

This decreases the mechanical strength of the solid electrolyte, the grain boundary resistance is increased, and the low-temperature deterioration occurs in the solid electrolyte under a state at a low temperature.

On the other hand, when the alumina content of the entire solid electrolyte exceeds 25 mass %, the particle sizes of the alumina grains are not uniform, and some alumina grains have a particle size which is the same or larger than that of the zirconia grains. Stress is concentrated into the alumina grains having the large particle size, and this generates cracks here. Therefore, this decreases the mechanical strength of the solid electrolyte, and there is a probability to decrease the resistance value of the solid electrolyte.

The solid electrolyte according to the present invention has a relative density of not less than 93%.

When the above relative density is less than 93%, it becomes difficult to form the grain boundaries of the zirconia grains with a high density. There is a probability of it being difficult to adequately obtain a high ion conductivity and a high thermal shock resistance. Further, there is a probability of it being difficult to adequately suppress the low-temperature deterioration of the solid electrolyte.

The method of producing the solid electrolyte according to the second aspect of the present invention has the first pulverizing step, the second pulverizing step, the first mixing step, the second mixing step, the molding step, and the firing step.

The first pulverizing step adds yttria as stabilizing agent (or stabilizer) into zirconia, then performs a dry-mixing to mix them, and pulverizes them to make a zirconia mixed powder. At this time, it is preferable to add 2 to 10 mol. % of yttria per zirconia content in the obtained solid electrolyte for use in a gas sensor.

It is preferred in the first pulverizing step for the zirconia powder to have a particle size of not more than 0.7 μm. This allows yttria to be efficiently dispersed in the zirconia powder.

The second pulverizing step adds a solvent into the zirconia mixed powder, and pulverizes the zirconia mixed powder having a large particle size. It possible to use, as the solvent, ethanol (ethyl alcohol), butanol (butyl alcohol), propanol, methyl isobutyl ketone, toluene, xylene, water, et al.

It is preferable to perform the second pulverizing step to make the zirconia powder having an average particle size of not more than 0.6 μm. This makes it possible for the zirconia grains to have a fine particle size, and to uniform the particle size of the zirconia grains in the solid electrolyte for use in a gas sensor. This obtains a dense grain boundaries of the zirconia grains in the solid electrolyte.

The first and second pulverizing steps pulverize the zirconia grains with a ball mill, a pearl mill, et al. The solvent is removed during a drying step and a degrease step. However, because the zirconia powder is cohered or condensed when the drying step is performed after completion of the second pulverizing step to obtain the zirconia powder, it is preferred to perform the first mixing step for the slurry, in which the zirconia grains are dispersed in the solvent, without performing any drying step after completion of the second pulverizing step. It is also possible to perform the drying step after completion of the second pulverizing step to obtain the zirconia powder, and then to go to the first mixing step.

In the first mixing step, alumina slurry containing alumina having an average particle size of not more than 0.5 μm is added into the zirconia powder, and mixed to made the intermediate material.

When the average particle size of the alumina, to be added into the alumina slurry, exceeds 0.5 μm, the effect to suppress growing the zirconia grains by the alumina is decreased, and as a result, the particle size of the zirconia grains become large, and the zirconium grains are not uniform. This generates gaps between the grain boundaries, and decreases the mechanical strength of the solid electrolyte, increases the grain boundary resistance, and deteriorates the characteristics of the solid electrolyte under a low temperature condition.

It is possible to use nano-order alumina grains or submicron order alumina grains to be added into the alumina slurry. It is preferable for the alumina grains to have the average particle size of not more than 50 μm when the nano-order alumina grains are used, and more preferable to have the average particle size of not more than 30 μm.

Although it is preferable for the alumina grains to have the average particle size as small as possible, the more the average particle size of the alumina grains decreases, the more the difficulty to make them increases. That is, there is a limitation of the average particle size of the alumina grains to be used for producing the solid electrolyte.

It is preferable to use alumina slurry in which alumina grains are uniformly dispersed when submicron-order alumina grains are used, and more preferable to have the average particle size of not more than 30 μm. The above alumina slurry can be obtained as follows.

The solvent such as ethanol is added into submicron-order alumina powder. The alumina powder is pulverized in a ball mil for four hours in order to pulverize the alumina grains having a large particle size. A predetermined amount of disperser is added into the alumina powder. The alumina powder is then mixed for 30 minutes with a high pressure homogenizer, where the disperser can uniformly disperse the alumina powder in the solvent. This state will be referred to as "alumina powder or grains in the primary-order particle state".

The reason why the homogenizer is used in this mixing step will be explained later.

It is preferred to add the alumina so that the alumina content becomes within a range of 5 to 25 mass % per the entire of the solid electrolyte for used in a gas sensor.

It is possible to perform the mixing step of mixing the zirconia powder and the alumina slurry with a ball mill, a pearl mill, or a wet-type jet mill.

As previously described, it is preferable for the solid electrolyte to have the thermal expansion coefficient which is approximately equal to that of the alumina. It is therefore preferable to adjust the thermal expansion coefficient of the solid electrolyte by adjusting the addition amount of alumina.

The second mixing step makes the slurry by adding binder and plasticizer into the intermediate material. It is possible to further add antifoamer in addition to the binder and the plasticizer. It is preferable to add several mass % of binder, plasticizer, and antifoamer to the intermediate material.

It is preferable to add disperser to disperse zirconia grains into the intermediate material. It is preferable for the homogenizer to mix the intermediate material and the dispersing agent. That is, the high pressure homogenizer generates shearing force to pulverize the adhered grains while blades of the high pressure homogenizer are passing through the slurry. Therefore the high pressure homogenizer does not have energy to pulverize the grains in the slurry. Therefore because the high pressure homogenizer does not pulverize the disperser as an additive, it is possible to adhere the disperser to the grains, and to efficiently and uniformly disperse the grains into the slurry.

It is possible to use cellulose, acrylic resin, polyvinyl, or polyvinyl butyral, et al., as the binder.

It is also possible to use ester phthalate, ester fatty acid, glycol derivative, et al., as the plasticizer.

It is also possible to use polyethylene glycol, et al. as antifoamer.

Those binder, the plasticizer, and the antifoamer are removed during the degrease step.

The shaping step (or molding step) expands the slurry to form the zirconia sheet. For example, zirconia sheet can be made by a doctor blade method.

The firing step fires the zirconia sheet to make the solid electrolyte to be used in a gas sensor.

The first step is performed at a high temperature within a range of 1450 to 1600° C. for a period within a range of 0.5 to 2 hours.

When the firing temperature increases, it is possible to easily transform the zirconia grains into C phase (cubic) having a large thermal expansion coefficient. As previously described, because it is better for the solid electrolyte to have the thermal expansion coefficient which is approximately equal to that of the alumina, it is preferable for the zirconia grains to avoid transforming into C phase as completely as possible. Therefore it is possible to perform the firing step at a temperature within a range of 1450 to 1550° C.

It is possible to adjust the average particle size Rz, Ra of the zirconia grains and the alumina grains in the solid electrolyte for use in a gas sensor by selecting an average particle size of raw material, a dispersing condition, and the firing temperature. For example, the more the average particle size of raw material increases, the more non-uniform becomes the dispersing state of the grains, and in addition the grains adhere together, the firing temperature becomes higher, and the average particle size Ra, Ra of the zirconia grains and the alumina grains after the firing step increases.

It is also possible to adjust the average distance value $A_{La}$ and the standard deviation $S_{La}$ of the average distance value by adjusting the adding amount of raw material, the dispersion state, and the firing temperature, etc. For example, the less the adding amount of raw is and the more the firing temperature is increased, the more the average distance value $A_{La}$ between grains becomes large. Further, when the dispersion state of the raw is not uniform, the standard deviation $S_{La}$ of the grain distance becomes large.

The dispersion state of the raw in the production of the solid electrolyte for a gas sensor affects the dispersion state of the grains after completion of the firing step. Therefore it is necessary to uniformly disperse the grains of raw in order to have a uniform dispersion state of the grains after completion of the firing step.

The dispersion state of the raw can be adjusted by kinds of dispersing agent and adding amount.

It is possible to select the optimum kind of the dispersing agent according to every type of grains of raw because the dispersion effect of the dispersing agent is changed based on the kind and the particle size of the dispersing agent.

It is sufficient to adjust the amount of the dispersing agent according to the function of the dispersing agent.

It is possible to efficiently and uniformly disperse the grains of raw material in the primary-order particle state (in which each of the grains is independently separated) by adding several mass % (for example, 2 mass %) of the dispersing agent per raw material even if the slurry containing a large amount (for example, 50 mass %) of solids is used when the dispersing agent with a good dispersion function is used.

Further, it is necessary to add the dispersing agent into the raw material within an optimum range of the amount of the dispersing agent in order to effectively show the dispersing effect thereof. When the adding amount of the dispersing agent is out of the optimum range, the grains of the raw material are adhered. This has a probability to deteriorate the uniform dispersing state of the grains in the raw material.

First Embodiment

A description will now be given of the solid electrolyte, for use in gas sensors, according to the first embodiment of the present invention with reference to FIG. 1 to FIG. 5, and Table 1.

In the first embodiment, thirteen types of solid electrolytes (E1 to E13) were prepared, and four types of comparison solid electrolytes (C1 to C4) were prepared. The solid electrolytes (E1 to E13, and C1 to C4) can be applied to gas sensors.

Figure 9:
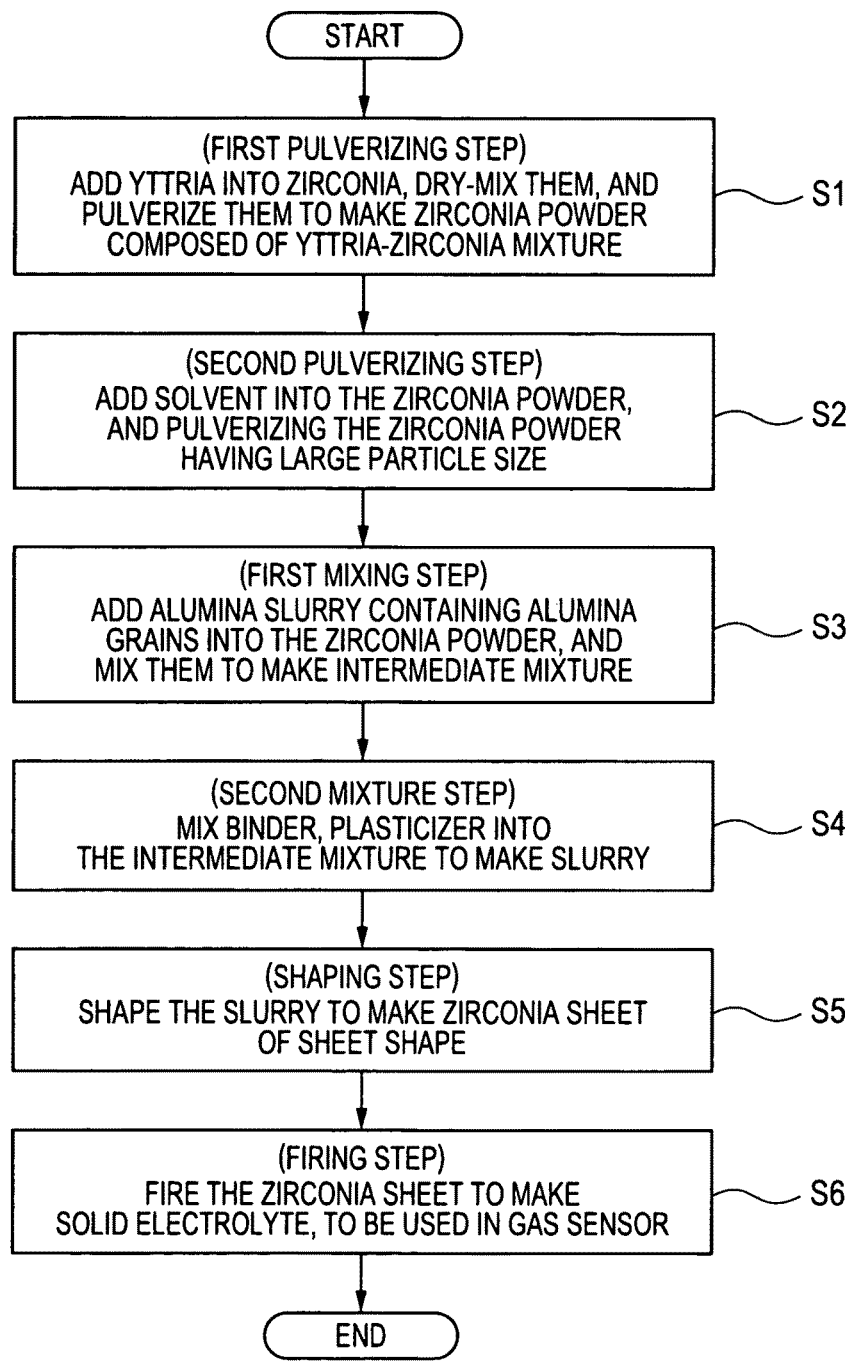
FIG. 9 is a flow chart showing a method of producing the solid electrolyte according to the present invention.

FIG. 9 is a flow chart showing a method of producing the solid electrolyte 1 according to the present invention.

Those solid electrolytes (E1 to E13, and C1 to C4), to be used in gas sensors, were produced by the method which is comprised of the first pulverizing step (S1), the second pulverizing step (S2), the first mixing step (S3), the second mixture step (S4), the shaping or molding step (S5), and the firing step (S6).

In the first pulverizing step (S1), approximately 6 mol. % of yttria was added into zirconia raw material, and they were dry-mixed together, and then pulverized to make zirconia powder. The first pulverizing step was performed to make the zirconia powder having an average particle size of 0.6 μm.

Next, in the second pulverizing step (S2), solvent such as ethanol was added into the zirconia powder. The zirconia powder dispersed in the solvent was pulverized with a ball mill for 24 hours. The second pulverizing step was performed so that the zirconia powder having an average particle size of 0.5 μm.

In the first mixing step (S3), a predetermined amount of alumina slurry (which has an average particle size of 30 nm manufactured by CIK Nano Tek Corporation.) was added into the zirconia powder to make an intermediate material so that each of the samples had an aluminum content shown in Table 1 (which will be shown later). In the alumina slurry, each of alumina grains was uniformly dispersed in the zirconia powder. In other words, each of alumina grains is independently separated. This state will also be referred to as the alumina grains "in a primary-order particle state". This aluminum content is a content of alumina in the entire of the solid electrolyte as a final product.

Although the first embodiment used nano-order alumina grains as alumina to be used in the alumina slurry, it is possible to use sub-micron order alumina grains. When sub-micron order alumina grains are used, the following alumina slurry is prepared in advance.

Specifically, solvent such as ethanol is added into alumina powder (which has an average particle size of 0.3 μm) of sub-micron order. The alumina powder is then pulverized for 24 hours with a ball mill in order to pulverize alumina grains having a large particle size. A disperser of 2 mass % (ED216 manufactured by Kusumoto Chemicals, Ltd.) is added into the pulverized alumina powder. This disperser can disperse the alumina grains in the alumina slurry having the alumina grains in the primary-order particle state. The alumina powder and the solvent are mixed for 30 minutes with a high pressure homogenizer to make the alumina slurry in which each of the alumina grains are uniformly dispersed.

In the second mixture step (S4), 2 mass % of the disperser (ED216 manufactured by Kusumoto Chemicals, Ltd.), 7.5 mass % of a binder (PVB), and 4.5 mass % of a plasticizer (Butylbenzyl phthalate) were added into the intermediate material, where the disperser uniformly disperses zirconia grains in the primary-order particle state in the intermediate material. The above mixture was mixed for one hour with a high pressure homogenizer. After this, the mixture was defoamed with a vacuum deaerator in order to make the slurry having a predetermined viscosity.

In the shaping step (S5), the slurry was shaped into a zirconia sheet having a sheet shape by using a doctor blade method. The zirconia sheet was dried, and degreased. In the firing step (S6), the zirconia sheet after shaping step, was finally fired at a firing temperature shown in the following Table 1 in order to produce the solid electrolyte (samples E1 to E13 and c1 to C4).

TABLE 1

| Sample No. | Firing temperature (° C.) | Alumina content (mass %) | Grain distance between alumina grains | | Particle size of Alumina grains | | Particle size of Zirconia grains | |
|---|---|---|---|---|---|---|---|---|
| | | | Average distance value $A_{La}$ (μm) | Standard deviation $S_{La}$ | Average particle size Ra (μm) | Standard deviation | Average particle size Rz (μm) | Standard deviation |
| E1 | 1600 | 5 | 1.65 | 0.71 | 0.35 | 0.24 | 1.93 | 0.97 |
| E2 | 1450 | 10 | 1.01 | 0.41 | 0.35 | 0.23 | 0.51 | 0.19 |
| E3 | 1500 | 10 | 1.19 | 0.50 | 0.36 | 0.25 | 0.69 | 0.36 |
| E4 | 1550 | 10 | 1.32 | 0.58 | 0.43 | 0.33 | 0.92 | 0.56 |
| E5 | 1600 | 10 | 1.53 | 0.60 | 0.48 | 0.34 | 1.62 | 0.80 |
| E6 | 1450 | 15 | 0.96 | 0.43 | 0.44 | 0.36 | 0.48 | 0.22 |
| E7 | 1500 | 15 | 1.15 | 0.51 | 0.46 | 0.33 | 0.57 | 0.27 |
| E8 | 1550 | 15 | 1.35 | 0.58 | 0.50 | 0.38 | 0.79 | 0.42 |
| E9 | 1600 | 15 | 1.45 | 0.58 | 0.58 | 0.40 | 1.32 | 0.56 |
| E10 | 1450 | 20 | 0.97 | 0.36 | 0.37 | 0.31 | 0.50 | 0.28 |
| E11 | 1500 | 20 | 1.17 | 0.47 | 0.46 | 0.37 | 0.57 | 0.26 |
| E12 | 1550 | 20 | 1.32 | 0.50 | 0.53 | 0.42 | 0.79 | 0.36 |
| E13 | 1600 | 20 | 1.42 | 0.55 | 0.55 | 0.49 | 1.08 | 0.57 |
| C1 | 1460 | — | — | — | — | — | 0.57 | 0.45 |
| C2 | 1600 | — | — | — | — | — | 8.69 | 4.68 |
| C3 | 1600 | 10 | 2.82 | 1.26 | 1.32 | 1.02 | 3.85 | 1.76 |
| C4 | 1600 | 5 | 2.40 | 1.44 | 0.84 | 0.67 | 7.15 | 3.37 |

| Sample No. | Low temperature deterioration test | Complex impedance (Ω) | | | Thermal expansion coefficient ($\times 10^{-8}$/° C.) | 3-point bending strength (Mpa) |
|---|---|---|---|---|---|---|
| | | Internal resistance of grains | Grain boundary resistance | Sum | | |
| E1 | ○ | — | — | — | — | 533 |
| E2 | ○ | 80.0 | 44.3 | 124.3 | 9.06 | 726 |
| E3 | ○ | 69.2 | 44.1 | 113.3 | 9.95 | 786 |
| E4 | ○ | 65.9 | 43.8 | 109.7 | 10.26 | 836 |
| E5 | ○ | 71.1 | 23.6 | 94.7 | 10.64 | 852 |

TABLE 1-continued

| | | | | | | |
|---|---|---|---|---|---|---|
| E6 | ○ | 87.9 | 46.5 | 134.4 | 8.62 | 684 |
| E7 | ○ | 74.0 | 41.6 | 115.6 | 9.34 | 873 |
| E8 | ○ | 66.0 | 44.4 | 110.4 | 10.01 | 844 |
| E9 | ○ | 66.0 | 37.2 | 103.2 | 10.13 | 916 |
| E10 | ○ | — | — | — | — | 770 |
| E11 | ○ | — | — | — | — | 798 |
| E12 | ○ | — | — | — | — | 892 |
| E13 | ○ | — | — | — | — | 800 |
| C1 | X | 62.0 | 86.2 | 148.2 | 9.30 | 454 |
| C2 | X | — | — | — | 10.55 | 390 |
| C3 | X | — | — | — | — | 387 |
| C4 | X | — | — | — | — | 401 |

The first embodiment measured a particle size of a zirconia grain, a particle size of an aluminum grain, and a distance between alumina grains of the produced solid electrolytes as the samples E1 to E13 and the comparison samples C1 to C4.

<Measurement of Particle Size of Zirconia Grain>

The particle size of zirconia grain was measured based on a SEM photograph of each of the solid electrolytes (E1 to E13 and C1 to C4). Specifically, each sample was polished, and thermally etched in order to clearly expose the crystal grain boundaries of the zirconia grains. The thermal etching was performed for 20 minutes at a temperature 200° C. below the firing temperature. A carbon film was deposited on the surface of each sample. In the observation of the SEM photograph, all of the zirconia grains shown on the SEM photograph at 10,000 times magnification in each sample were traced by using image processing software. A diameter of a circle corresponding to each zirconia grain was measured. An average particle size and a standard deviation of the zirconia grains were then calculated. Those measurement and calculations were performed on three microscope fields in order to calculate the average value and the standard deviation of them. Table 1 shows the results (the average particle size Rz and the standard deviation) of the above observation and calculations.

<Measurement of Particle Size of Alumina Grain)

The particle size of an alumina grain was measured by observation of the SEM photograph of each sample which was coated with a deposited carbon film. The SEM photograph was previously used to measure the particle size of the zirconia grain previously described. Since the black part on the reflected electron images on the SEM photograph at 10,000 times magnification corresponds to alumina particles, binarization of the SEM photograph was performed by using the image processing software in order to select the black parts. After completion of the binarization process, the diameter of each alumina grain corresponding to a circular shape was detected in the binarized image data, and the average value and the standard deviation of them were calculated. It is possible to change the magnification of the SEM photograph according to demands. Those measurement and calculations were performed on three microscope fields in order to calculate the average value and the standard deviation of them (such as the average particle size Ra and the standard deviation). Table 1 shows the results of the above observation and calculations.

<Measurement of Distance Between Alumina Grains>

The distance between alumina grains was measured by observation of the SEM photograph of each sample which was coated with a deposited carbon film. The SEM photograph was used to measure the particle size of the zirconia grain, as previously described. Since the black part on the reflected electron images on the SEM photograph of 10,000 magnification corresponds to the alumina particle, the distance between central points of adjacent black parts was measured. The observation of the distance between the adjacent alumina grains was performed for all of the alumina grains. The average value and the standard deviation of them were calculated. The above measurement and calculations were performed on three microscope fields in order to calculate the average value and the standard deviation of them (such as the average distance value $A_{La}$ and the standard deviation $S_{La}$). Table 1 shows the results of the above observation and calculations.

As can be seen from the measurement and detection results shown in FIG. 1, each of the solid electrolytes according to the present invention (which correspond to the samples E1 to E13) is a solid electrolyte in which fine alumina grains are dispersed in at least grain boundaries of zirconia grains containing yttria as stabilizing agent.

The zirconia grains in the samples E1 to E13 as the solid electrolytes have the average particle size Rz of not more than 2 μm. The alumina grains in the samples E1 to E13 as the solid electrolytes according to the present invention have the average particle size Ra of not more than 1 μm. Thus, the average particle size Ra of the alumina grain is smaller than the average particle size Rz of the zirconia grain.

The average distance value $A_{La}$ between the alumina grains is not more than 2 μm, and the standard deviation $S_{La}$ of them is not more than 0.8.

Figure 2:
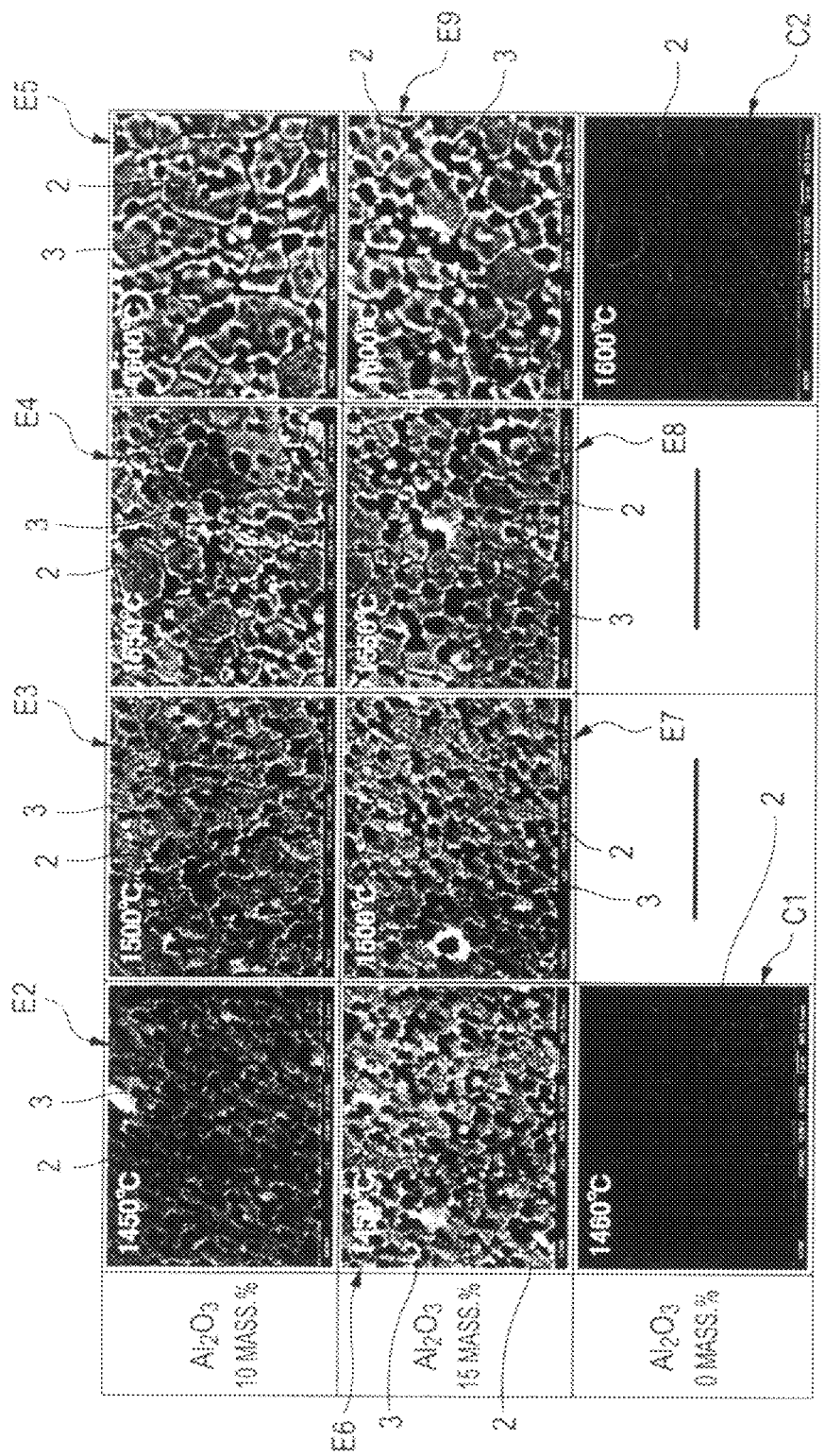
FIG. 2 shows SEM photographs of samples E2 to E9 (as solid electrolytes according to the present invention) and comparison samples C1 and C2 (as conventional solid electrolyte), showing experimental results of the first embodiment of the present invention.

FIG. 1 is a SEM photograph of the sample E7 as the solid electrolyte according to the first embodiment of the present invention. FIG. 2 are SEM photographs of the samples E2 to E9 as the solid electrolytes and comparison samples C1 and C2 of solid electrolytes, which are experimental results in the first embodiment of the present invention.

As shown in FIG. 1 and FIG. 2, it can be understood from the observation results that the particle size of the zirconia grain 2 becomes large, and the zirconia grains do not have a uniform particle size and are not uniformly dispersed in the solid electrolyte when the solid electrolyte only contains zirconia grains without any alumina grains.

On the other hand, it can be understood from the observation results that the particle size of the zirconia grains becomes small and the zirconia grains have a uniform particle size, and are uniformly dispersed in the solid electrolyte when the alumina grains 3 having a fine particle size are dispersed in the zirconia grains 2.

Next, a description will be given of the experimental results of the samples E1 to E13 and the comparison samples C1 to C3 in the low-temperature deterioration test under a condition at a low temperature, the calculation of a complex impedance, the 3-point bending test, and the calculation of the thermal expansion coefficient.

<Low-Temperature Deterioration Test>

A hydrothermal treatment of each of the samples was performed at a temperature of 230° C. for 10 hours with an autoclave. After completion of the hydrothermal treatment, it was detected using a stain solution whether or not there are cracks in the samples which were caused by a phase transition of the crystal phase from C phase (cubic) to M phase (monoclinic phase). In Table 1, reference character "◯" indicates absence of cracks, and a reference character "X" indicates the presence of cracks.

The samples E1 to E13 do not have any defect. That is, there are no parts which were stained by the stain solution. Because the zirconia grains have a fine particle size in the samples E1 to E13, this suppress the occurrence of the phase transition in the crystal phase of the zirconia grains, or suppresses the occurrence to generate a fine crack even if the phase transition occurs therein. The observation results indicate that the solid electrolyte, to be applied to gas sensors, according to the present invention can suppress a deterioration of the solid electrolyte even if it is placed at a low temperature.

On the other hand, stained parts were observed in the comparison samples C1 to C4, and cracks were detected or observed therein. This means that the cracks were generated by the phase transition from T phase (tetragonal) to M phase (monoclinic). This is because this phase transition causes a volume expansion of approximately 4% and such a fine crack was generated at the grain boundaries of the zirconia grains.

<Detection of Complex Impedance>

Ag electrodes were formed on both the surfaces of each sample. This sample to be detected is a pellet having a thickness t=0.4 mm, and a diameter φ=16 mm. The pellet with the Ag electrodes was detected under the condition at 500° C. in atmosphere using detection frequency within a range from direct current to 1 MHz.

Figure 3:
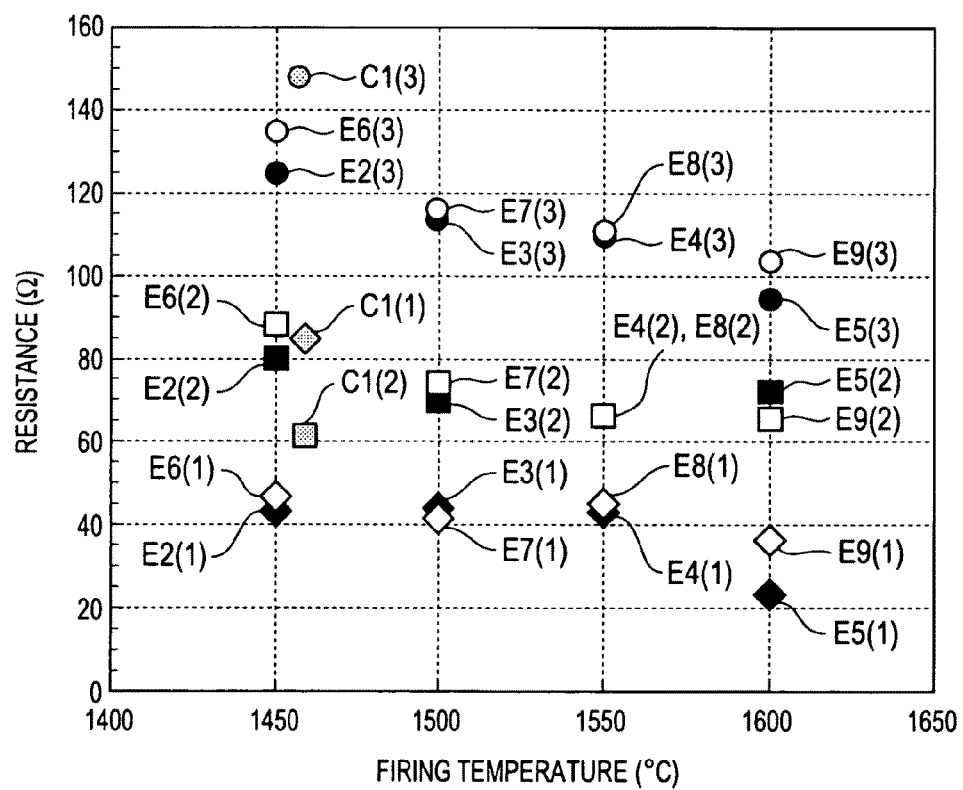
FIG. 3 is a graph showing a complex impedance of each of the samples E2 to E9 and the comparison samples C1 and C2 as experimental results of the first embodiment of the present invention.

FIG. 3 is a graph showing a complex impedance of each of the samples E2 to E9 and the comparison sample C1 and C2 as the experimental results in the first embodiment of the present invention. In FIG. 3, the horizontal axis indicates the temperature (° C.), and the vertical axis indicates the resistance (Ω). In FIG. 3, reference characters E2 to E9 and C1 and C2 represent the detection results of the samples E2 to E9, and the comparison samples C1 and C2, respectively.

Further, in FIG. 3, the reference character "(1)" designates the grain boundary resistance of the sample, the reference character "(2)" indicates an internal grain resistance of the sample, and the reference character "(3)" denotes a sum of the grain boundary resistance and the internal grain resistance of the sample. That is, the reference character "(3)" indicates the resistance of the solid electrolyte.

When the detection results of the samples E2 to E9 are compared with the detection result of the sample C1, FIG. 3 clearly shows that the dispersion of the alumina grains into the zirconia grains increases the internal grain resistance, but drastically decreases the grain boundary resistance.

Because the samples E2 to E9 contain the zirconia grains of a fine particle size, this suppresses generating fine cracks therein even if the crystal phase is transformed. Thus, this decreases the grain boundary resistance of each of the samples e2 to E9.

On the other hand, the sample C1 has a low density in the grain boundary area, and the grain boundary resistance is thereby increased. Even if the alumina grains are dispersed in the zirconia grains.

It is thereby possible for the sum of the internal grain resistance and the grain boundary resistance in each of the samples E2 to E9 to be not more than that of the sample C1.

It is therefore possible for the present invention to provide the solid electrolyte having a high ion conductivity which can be used in gas sensors.

<Measurement of 3-Point Bending Strength>

In the measurement to measure a 3-point bending strength of each sample, a plurality of the solid electrolyte of a sheet shape was stacked and pressed by a cold isostatic press (CIP) at 85° C. and 85 MPa so that the solid electrolyte lamination had a thickness of approximately 4 mm. The solid electrolyte lamination was cut to make samples having a width of 5 mm and a length of 45 mm. The samples were degreased at 500° C. over 25 hours. The temperature was gradually increased to 500° C. over five days. The degreased sample was heated to a predetermined temperature in an electric furnace by the rising speed of 150° C./hour, and kept at the predetermined temperature for one hour to fire the sample. The strength evaluation sample was prepared, and the 3-point bending test was performed for the fired samples based on R1601 of Japanese Industrial Standard (JIS). The 3-point bending test was performed four times every sample. The Table 1 shows the average value of the 3 point bending strength of each sample.

There is no problem in use when the solid electrolyte has the 3-point bending strength of not less than 500 MPa.

Figure 4:
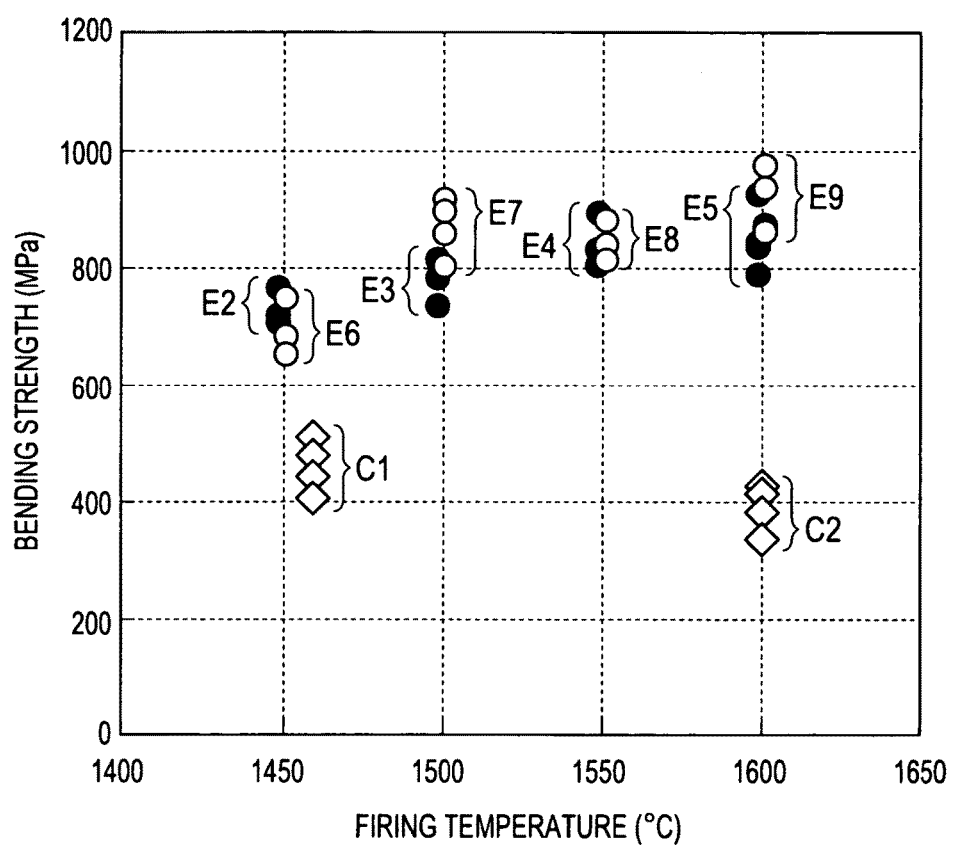
FIG. 4 is a graph showing a 3-point bending strength of each of the samples E2 to E9 and the comparison samples C1 and C2 as the experimental results of the first embodiment of the present invention.

FIG. 4 is a graph showing a 3-point bending strength (or flexural strength) of each of the samples E2 to E9 and the comparison samples C1 and C2 as the experimental results in the first embodiment of the present invention. In FIG. 4, reference characters "E2 to E9" and "C1 and C2" designate the detection results of the samples E2 to E9 and C1 and C2, respectively.

As can be understood from the detection results shown in FIG. 4, each of the samples E2 to E9 is higher in 3-point bending strength (or flexural strength) than each of the comparison samples C1 and C2. The solid electrolyte, to be used in gas sensors, according to the present invention has a high thermal shock resistance when compared with the conventional solid electrolyte.

<Detection of Thermal Expansion Coefficient>

The thermal expansion coefficient of each sample was detected, by TMA-60H manufactured by Shimadzu Corporation, based on a differential thermal expansion using alumina as comparison samples.

The sample had a length of 10 mm, and a temperature detection range is from room temperature to 1000° C., and the average value of the thermal expansion coefficient was calculated within the temperature range of room temperature to 1000° C. The measurement of the thermal expansion coefficient was performed three times per sample. Table 1 shows the average value of the thermal expansion coefficient in each sample.

Figure 5:
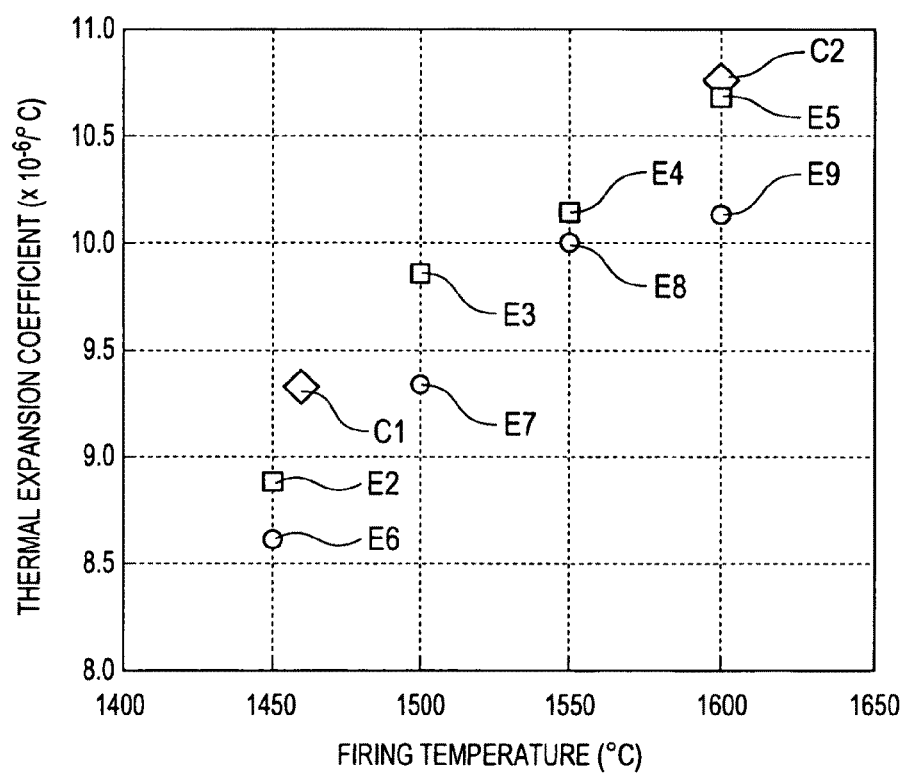
FIG. 5 is a graph showing an average value of the detected thermal expansion coefficients of each of the samples E2 to E9 and the comparison samples C1 and C2 as the experimental results in the first embodiment of the present invention.

FIG. 5 is a graph showing the average value of three detections of the a thermal expansion coefficient of each of the samples E2 to E9 and the comparison samples C1 and C2 as the experimental results in the first embodiment of the present invention.

In FIG. 5, the horizontal axis indicates the firing temperature (° C.), and the vertical axis indicates the thermal expansion coefficient ($\times 10^{-6}$/° C.). In FIG. 5, reference characters "E2" to "E9" and "C1" and "C2" designate the detection results (average value) of the samples E2 to E9 and the comparison samples C1 and C2, respectively.

It can be understood from the detection results shown in FIG. 5 that the thermal expansion coefficient becomes small according to increasing of the alumina content in the sample.

Because increasing of the firing temperature easily causes the phase transition of the zirconia grains to C phase (cubic), this increases the thermal expansion coefficient.

Because the solid electrolyte (zirconia grains) and alumina grains are fired together, it is preferable for the solid electrolyte to have a thermal expansion coefficient which is approximately equal to that of the alumina grains. It is therefore preferable to adjust the thermal expansion coefficient of the solid electrolyte (as the zirconia grains) by adjusting the alumina content and the firing temperature.

As described above in detail, the first embodiment provides the solid electrolyte having a high ion conductivity and a high thermal expansion coefficient, capable of suppressing the low-temperature deterioration even if used at a low temperature. The first embodiment also provides the optimum method of producing the solid electrolyte having the above features.

Second Embodiment

A description will now be given of the solid electrolyte, for use in gas sensors, according to the second embodiment of the present invention with reference to table 2 and FIG. 1 to FIG. 5.

Figure 6:
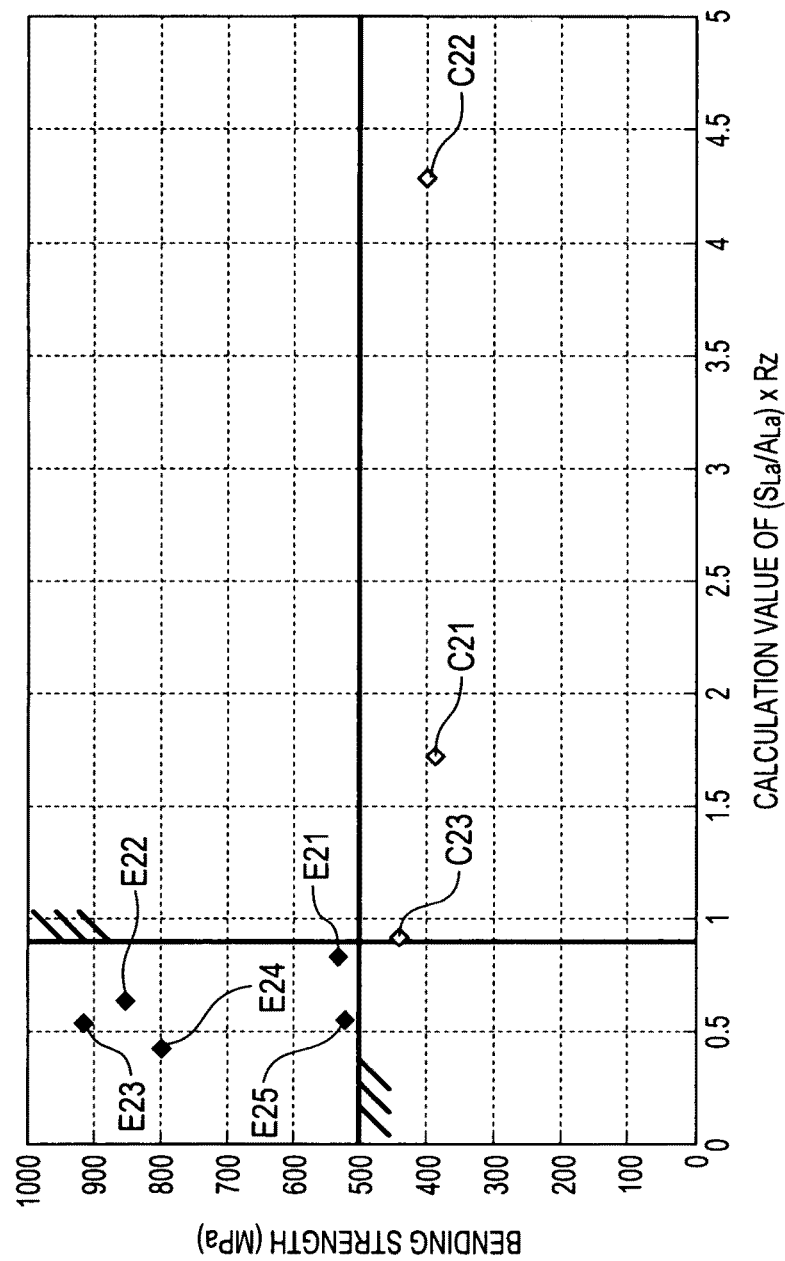
FIG. 6 is a graph showing a relationship between calculation value of $(S_{La}/A_{La} \times Rz)$ and 3-point bending strength as the experimental results of a second embodiment of the present invention.

FIG. 6 is a graph showing a relationship between calculation values and flexural strength as the detection results in the second embodiment of the present invention.

As shown in following Table 2 and FIG. 6, the second embodiment detected the thermal shock resistance of the solid electrolyte in two cases, one satisfied, and the other did not satisfy the following relationship (1):

$$(S_{La}/A_{La}) \times Rz \leq 0.9 \quad (1),$$

where Rz is the average particle size of zirconia grains, $A_{La}$ is the average distance value between adjacent alumina grains, and $S_{La}$ is the standard deviation of the average distance value $A_{La}$ between the alumina grains.

As shown in Table 2, the second embodiment prepared samples E21 to E25 which satisfied the relationship (1), and comparison samples C21 to C23 which did not satisfy the relationship (1).

The second embodiment used the same method of the first embodiment of producing the solid electrolyte. The second embodiment used the firing temperature of 1600° C., and 6 mol. % of yttria per zirconia grains.

As shown in table 2, the samples E21, E22, E23, and E24 were equal in content and feature to the samples E1, E5, E9, and E13 used in the first embodiment. The comparison samples C21 and C22 were equal in content and feature to the samples C3 and C4 used in the first embodiment.

Table 2 shows the calculation value which corresponds to the value of $(S_{La}/A_{La}) \times Rz$ (which is the same in Table 3 to Table 6 described later). The calculation value of not more than 0.9 satisfies the relationship (1). The calculation value of more than 0.9 does not satisfy the relationship (1).

The second embodiment detected a 3-point bending strength of each of the samples E21 to E25 and C21 to C23 by the same method of the first embodiment. The detection results are shown in Table 2 and FIG. 6. FIG. 6 shows the relationship between the calculation values and the 3-point bending strength (MPa).

It can be seen from the detection results shown in Table 2 and FIG. 6 that each of the samples E21 to E25 according to the present invention has the 3-point bending strength of not less than 500 MPa which satisfies the common use.

On the other hand, each of the comparison samples C21 to C23 has the bending strength of less than 500 MPa which is lower than that of each of the samples E21 to E25 according to the present invention.

As can be seen from Table 2 and FIG. 6, the particle size Rz of zirconia grains, the average distance value $A_{La}$ between the alumina grains, and the standard deviation SLa of the samples C21 to C23 are large when compared with those of the samples E21 to E25. Therefore because the particle size of the zirconia grains is large and the alumina grains are not uniformly dispersed in the grain boundaries of the zirconia grains, the samples C21 to C23 as the solid electrolyte have a decreased mechanical strength.

Accordingly, it is possible for the solid electrolyte to obtain a mechanical strong strength when it is produced to satisfy the relationship (1): $(S_{La}/A_{La}) \times Rz \leq 0.9 \ldots (1)$. Satisfying the relationship (1) increases the mechanical strength of the solid electrolyte, and can provides the solid electrolyte with a high thermal shock resistance.

Third Embodiment

A description will now be given of the solid electrolyte, for use in gas sensors, according to the third embodiment of the present invention with reference to Table 3.

The third embodiment detected the thermal shock resistance of the solid electrolyte when the alumina content therein is changed. Table 3 shows the detection results of the thermal shock resistance of samples E31, E32, E33, and E34, and comparison samples C31 and C32.

The samples E31 to E35 have the alumina contents within a range of 5 to 25 mass %. On the other hand, the comparison samples C31 and C32 have the alumina contents other than the range of 5 to 25 mass %.

The third embodiment used the same method of the first embodiment to produce the samples as the solid electrolyte. The third embodiment used the firing temperature of 1600° C. In the third embodiment, the solid electrolyte as the samples contained 6 mol. % of yttria per zirconia content.

The samples E31, E32, E33, and E34 used in the third embodiment were equal in contents and features to the samples E1, E5, E9, and E13, respectively.

TABLE 2

| Sample No. | Alumina content (mass %) | Grain distance between alumina grains | | Particle size of Alumina grains | | Particle size of Zirconia grains | | Relative density (%) | Calculation value of $(S_{La}/A_{La}) \times Rz$ | 3-point bending strength (Mpa) |
|---|---|---|---|---|---|---|---|---|---|---|
| | | Average distance value $A_{La}$ (µm) | Standard deviation $S_{La}$ | Average particle size Ra (µm) | Standard deviation | Average particle size Rz (µm) | Standard deviation | | | |
| E21 | 5 | 1.65 | 0.71 | 0.35 | 0.24 | 1.93 | 0.97 | 92 | 0.83 | 533 |
| E22 | 10 | 1.53 | 0.60 | 0.48 | 0.33 | 1.62 | 0.80 | 98 | 0.64 | 852 |
| E23 | 10 | 1.45 | 0.58 | 0.58 | 0.40 | 1.32 | 0.56 | 98 | 0.53 | 916 |
| E24 | 10 | 1.42 | 0.55 | 0.55 | 0.49 | 1.08 | 0.57 | 97 | 0.42 | 800 |
| E25 | 10 | 1.40 | 0.80 | 0.71 | 0.52 | 0.96 | 0.74 | 95 | 0.55 | 521 |
| C21 | 10 | 2.82 | 1.26 | 1.32 | 1.02 | 3.85 | 1.76 | 97 | 1.72 | 387 |
| C22 | 5 | 2.40 | 1.44 | 0.48 | 0.67 | 7.15 | 3.37 | 96 | 4.29 | 401 |
| C23 | 6 | 1.97 | 0.82 | 0.41 | 0.29 | 2.20 | 1.12 | 98 | 0.92 | 439 |

TABLE 3

| Sample No. | Alumina content (mass %) | Grain distance between alumina grains | | Particle size of Alumina grains | | Particle size of Zirconia grains | | Relative density (%) | Calculation value | 3-point bending strength (Mpa) |
|---|---|---|---|---|---|---|---|---|---|---|
| | | Average distance value $A_{La}$ (μm) | Standard deviation $S_{La}$ | Average particle size Ra (μm) | Standard deviation | Average particle size Rz (μm) | Standard deviation | | | |
| E31 | 6 | 1.65 | 0.71 | 0.35 | 0.24 | 1.93 | 0.97 | 97 | 0.83 | 533 |
| E32 | 10 | 1.53 | 0.60 | 0.48 | 0.34 | 1.62 | 0.80 | 98 | 0.64 | 852 |
| E33 | 15 | 1.45 | 0.58 | 0.58 | 0.40 | 1.32 | 0.56 | 98 | 0.53 | 916 |
| E34 | 20 | 1.42 | 0.55 | 0.55 | 0.49 | 1.08 | 0.57 | 97 | 0.42 | 800 |
| E35 | 25 | 1.40 | 0.80 | 0.71 | 0.52 | 0.96 | 0.74 | 95 | 0.55 | 521 |
| C31 | 2 | 2.03 | 0.84 | 0.32 | 0.22 | 2.34 | 1.12 | 98 | 0.97 | 436 |
| C32 | 30 | 1.41 | 0.84 | 0.82 | 0.68 | 0.92 | 0.80 | 94 | 0.55 | 489 |

The third embodiment measured the 3-point bending strength of each of the samples E31 to E35 and C31 and C32 by the same method of the first embodiment. Table 3 shows the measurement results.

Table 3 shows that the samples E31 to E35 as the solid electrolytes produced by the method according to the present invention have the bending strength of not less than 500 MPa which is no problem in use.

On the other hand, the comparison samples C31 and C32 have the bending strength of less than 500 MPa which is not adequate in use. This means that the comparison sample having the alumina content of less than 5 mass % cannot adequately suppress a crystal growth of the zirconia grains, and this decreases the mechanical strength of the solid electrolyte. In addition, when the alumina content exceeds 25 mass %, because it becomes difficult to uniformly disperse alumina grains, the mechanical strength of the solid electrolyte is decreased.

It is therefore possible to provide the solid electrolyte with a high mechanical strength and a high thermal shock resistance when the alumina content is set within the range of 5 to 25 mass % in the solid electrolyte.

Fourth Embodiment

A description will now be given of the solid electrolyte, for use in gas sensors, according to the fourth embodiment of the present invention with reference to Table 4.

As shown in Table 4, the fourth embodiment detected the thermal shock resistance of each of the samples E41, E42, and E43 and C41 and C42 when a yttria content was changed.

In the fourth embodiment, as shown in Table 4, the samples E41, E42, and E43 and the comparison samples C41 and C42 having a different yttria content per zirconia content. That is, the samples E41, E42, and E43 have the yttria content within a range of 2 to 10 mol. %. On the other hand, the comparison samples C41 and C42 have the yttria content other than the range of 2 to 10 mol. %.

The samples E41, E42, and E43 and the comparison samples C41 and C42 were produced by the same method of the first embodiment. Table 4 shows the detection results. The fourth embodiment used the firing temperature of 1600° C. The sample E42 was equal in content and feature to the sample E7 used in the first embodiment.

TABLE 4

| Sample No. | Yttria content (mass %) | Alumina content (mass %) | Grain distance between alumina grains | | Particle size of Alumina grains | | Particle size of Zirconia grains | | Relative density (%) | Calculation value | 3-point bending strength (Mpa) |
|---|---|---|---|---|---|---|---|---|---|---|---|
| | | | Average distance value $A_{La}$ (μm) | Standard deviation $S_{La}$ | Average particle size Ra (μm) | Standard deviation | Average particle size Rz (μm) | Standard deviation | | | |
| E41 | 2 | 15 | 0.93 | 0.41 | 0.38 | 0.27 | 0.49 | 0.20 | 97 | 0.22 | 666 |
| E42 | 6 | 15 | 1.15 | 0.51 | 0.46 | 0.33 | 0.57 | 0.27 | 97 | 0.25 | 873 |
| E43 | 10 | 15 | 1.42 | 0.67 | 0.53 | 0.36 | 0.76 | 0.51 | 97 | 0.36 | 627 |
| C41 | 1.6 | 15 | 0.91 | 0.41 | 0.39 | 0.26 | 0.51 | 0.23 | 96 | 0.23 | 201 |
| C42 | 12 | 15 | 1.83 | 1.01 | 0.61 | 0.42 | 2.12 | 1.04 | 97 | 1.17 | 465 |

The fourth embodiment detected the 3-point bending strength of each of the samples E41, E42, and E43 and the comparison samples C41 and C42 by the same method used in the first embodiment. Table 4 shows the detection results.

It can be seen from the detection results shown in Table 4 that the samples E41 to E43 according to the present invention have the bending strength of not less than 500 MPa which causes no problem in use.

On the other hand, the comparison samples C41 and C42 have the bending strength of less than 500 MPa, which is lower than that of the samples E41 to E43. The reason why the mechanical strength is decreased is the volume change which was occurred in the comparison samples C41 and C42 having the yttria content of less than 2 mol. % when the zirconia grains were transformed from T phase (tetragonal phase) to M phase (monoclinic phase).

Because the zirconia grains were changed in C phase (cubic) when the yttria content exceeded 10 mol. %, the zirconia grains easily grown in C phase and the mechanical strength of each of the comparison samples C41 and C42 was decreased even if the alumina grains were added into the zirconia grains during the production of the comparison samples C41 and C42.

According to the detection results of the fourth embodiment, it can be understood for the solid electrolyte to have an increased mechanical strength and a high thermal shock resistance by using the yttria content within a range of 2 to 10 mol. % per zirconia content.

Fifth Embodiment

A description will now be given of the solid electrolyte, for use in gas sensors, according to the fifth embodiment of the present invention with reference to Table 5.

Fifth embodiment detected the effect to suppress the low-temperature deterioration and the effect of an ion conductivity in various types of samples which include the samples having dispersed alumina grains, and a comparison sample without any alumina grain, that is, no alumina grain is dispersed.

The fifth embodiment produced the samples E51 to E58 having the alumina grains dispersed in zirconia grains, and the comparison sample C51 having no alumina grains in zirconia grains.

The fifth embodiment used the same method of the first embodiment to produce those samples. The fifth embodiment used the firing temperature of 1600° C. The solid electrolyte as the samples contained 6 mol. % of yttria per zirconia content.

The samples E51, E52, E53, E54, E55, E56, E57, and E58 were equal in content and feature to the samples E2, E3, E4, E5, E6, E7, E8, and E9 used in the first embodiment, respectively.

crack. Those samples E51 to E58 are designated by using the symbol "○" in Table 5. This means that those samples E51 to E58 have fine alumina grains having a fine particle size and the presence of the alumina grains of a fine particle size suppresses the phase transition of the crystal phase of the zirconia grains. Even if the phase transition occurred in the samples E51 to E58, the presence of the alumina grains of a fine particle size suppresses generating of a fine crack in the samples E51 to E58.

On the other hand, the comparison sample C51 has the part which was stained by the stain solution, and has a crack, designated by the symbol "X" in Table 5. It can be understood that the crack was generated in the comparison sample C51 by the volume expansion which was caused by the phase transition of the zirconia grains from T phase (tetragonal phase) to M phase (monoclinic phase).

In the samples E51 to E58, although the internal resistance of the grains was increased by dispersing the alumina grains into the zirconia grains, the grain boundary resistance of the zirconia grains was drastically decreased by dispersing the alumina grains in the grain boundaries of the zirconia grains. Therefore the sum of the internal grain resistance and the grain boundary resistance of each of the samples E51 to E58 becomes low when compared with the sum of them in the sample C51.

In addition, as can be seen from table 5, the samples E51 to E58 have the bending strength of not less than 500 MPa which is no problem in use.

TABLE 5

| Sample No. | Firing temperature (° C.) | Alumina content (mass %) | Grain distance between alumina grains | | Particle size of Alumina grains | | Particle size of Zirconia grains | |
|---|---|---|---|---|---|---|---|---|
| | | | Average distance value $A_{La}$ (μm) | Standard deviation $S_{La}$ | Average particle size Ra (μm) | Standard deviation | Average particle size Rz (μm) | Standard deviation |
| E51 | 1450 | 10 | 1.01 | 0.41 | 0.35 | 0.23 | 0.51 | 0.19 |
| E52 | 1500 | 10 | 1.19 | 0.50 | 0.36 | 0.25 | 0.69 | 0.36 |
| E53 | 1550 | 10 | 1.32 | 0.58 | 0.43 | 0.33 | 0.92 | 0.56 |
| E54 | 1600 | 10 | 1.53 | 0.60 | 0.48 | 0.34 | 1.62 | 0.80 |
| E55 | 1450 | 15 | 0.96 | 0.43 | 0.44 | 0.35 | 0.48 | 0.22 |
| E56 | 1500 | 15 | 1.15 | 0.51 | 0.46 | 0.33 | 0.57 | 0.27 |
| E57 | 1550 | 15 | 1.35 | 0.58 | 0.50 | 0.38 | 0.79 | 0.42 |
| E58 | 1600 | 15 | 1.45 | 0.58 | 0.58 | 0.40 | 1.32 | 0.56 |
| C51 | 1460 | 0 | — | — | — | — | 0.57 | 0.45 |

| Sample No. | Relative density (%) | Calculation value | Low temperature deterioration test | Complex impedance (Ω) | | | 3-point bending strength (Mpa) |
|---|---|---|---|---|---|---|---|
| | | | | Internal resistance of grains | Grain boundary resistance | Sum | |
| E51 | 95 | 0.21 | ○ | 80.0 | 44.3 | 124.3 | 726 |
| E52 | 96 | 0.29 | ○ | 69.2 | 44.1 | 113.3 | 786 |
| E53 | 97 | 0.40 | ○ | 65.9 | 43.81 | 109.7 | 836 |
| E54 | 98 | 0.64 | ○ | 71.1 | 23.6 | 94.7 | 852 |
| E55 | 95 | 0.22 | ○ | 87.9 | 46.5 | 134.4 | 684 |
| E56 | 97 | 0.25 | ○ | 74.0 | 41.6 | 115.6 | 873 |
| E57 | 98 | 0.34 | ○ | 66.0 | 44.4 | 110.4 | 844 |
| E58 | 98 | 0.53 | ○ | 66.0 | 37.2 | 103.2 | 916 |
| C51 | 95 | — | X | 62.0 | 86.2 | 148.2 | 454 |

The fifth embodiment detected the function of suppressing the low-temperature deterioration, the complex impedance, and the 3-point bending strength of each of the samples E51 to E58 and the comparison sample C51 by the same method of the first embodiment. Table 5 shows the detection results according to the fifth embodiment.

As can be seen from the detection results shown in Table 5, the samples E51 to E58 according to the present invention have no part which was stained by a stain solution and no On the other hand, the comparison sample C51 has the bending strength of less than 500 MPa, which are lower than that of the samples E51 to E58. This means that the comparison sample C51 has no function of suppressing growing of the zirconia grains, and the mechanical strength thereof is decreased.

According to the detection results of the fifth embodiment, it can be understood that the solid electrolyte can have a function of suppressing the low-temperature deterioration, and have a high ion conductivity by dispersing alumina grains into zirconia grains in the solid electrolyte. It is thereby possible for the solid electrolyte to have a high mechanical strength and a high thermal shock resistance.

Sixth Embodiment

A description will now be given of the solid electrolyte, for use in gas sensors, according to the sixth embodiment of the present invention with reference to Table 6.

The sixth embodiment detected the thermal shock resistance of samples E61, E62, and E63, and a comparison sample C61 as solid electrolytes which have alumina grains of a different particle size (or a raw particle size) which were mixed with zirconia powder (that is, zirconia grains) and dispersed in the zirconia grains.

The sixth embodiment, as shown in Table 6, produced the samples as the solid electrolytes having a different particle size of alumina raw grains. That is, the samples E61 to E63 according to the present invention had the alumina grains having the particle size of not more than 0.5 μm, and the comparison sample E61 had the alumina grains having the particle size of exceeding 0.5 μm.

The sixth embodiment used the same method of the first embodiment to produce those samples. The sixth embodiment used the firing temperature of 1600° C. and the yttria content of 6 mol. % per zirconia content.

The sample E61 was equal in content and feature to the samples E9 used in the first embodiment.

1.5 μm, and the standard deviation $S_{La}$ a within a range of 0.5 to 0.6. This condition better disperses alumina grains into the grain boundaries of the zirconia grains in the solid electrolyte, and provides excellent characteristics such as an excellent reduced grain boundary resistance.

Seventh Embodiment

A description will now be given of the solid electrolyte, for use in gas sensors, according to the seventh embodiment of the present invention with reference to FIG. 7 and FIG. 8.

Figure 7:
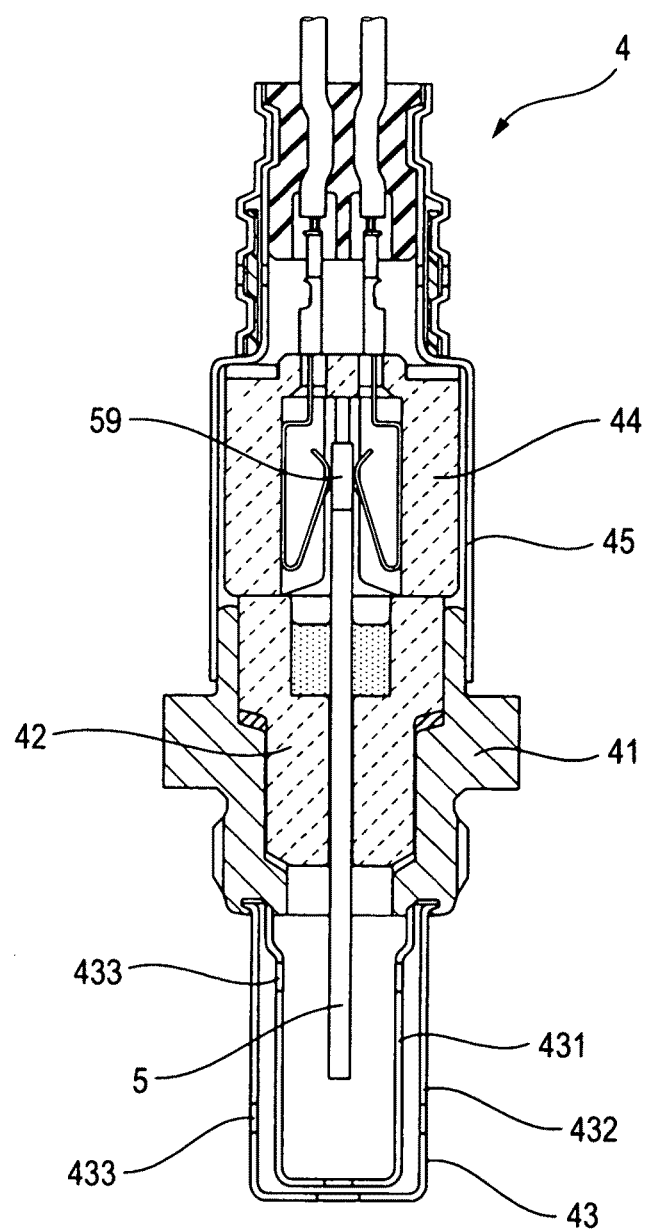
FIG. 7 is a view showing a gas sensor according to a seventh embodiment of the present invention.

FIG. 7 is a view showing a gas sensor according to the seventh embodiment of the present invention. FIG. 8 is a view showing the gas sensor element in the gas sensor according to the seventh embodiment of the present invention.

Figure 8:
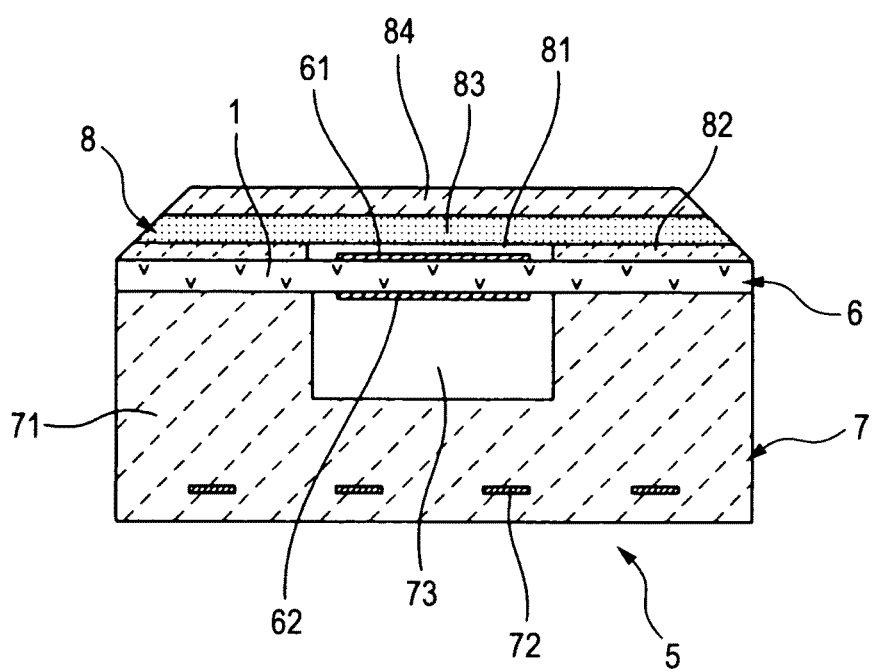
FIG. 8 is a view showing a gas sensor element equipped with the solid electrolyte to be used in the gas sensor according to the seventh embodiment of the present invention.

As shown in FIG. 7 and FIG. 8, the seventh embodiment provides the gas sensor 4 equipped with the solid electrolyte 1 according to the first embodiment.

The gas sensor 4 according to the seventh embodiment is comprised of a gas sensor element 5, a housing case 41, and an element cover 43. The gas sensor element 5 is inserted into and supported by the inside of the housing case 41. The element cover 43 is fixed to the housing case 41. The front part of the gas sensor element 5 is covered with the element cover 43. The gas sensor element 5 has a pair of an electrode 61 (which serves as the target gas detection electrode) and an electrode 62 (which serves as a reference gas electrode) formed on the surfaces of the solid electrolyte 1. This solid

TABLE 6

| Sample No. | Particle size (μm) of alumina raw | Alumina content (mass %) | Grain distance between alumina grains | | Particle size of Alumina grains | | Particle size of Zirconia grains | | Relative density (%) | Calculation value | 3-point bending strength (MPa) |
|---|---|---|---|---|---|---|---|---|---|---|---|
| | | | Average distance value $A_{La}$ (μm) | Standard deviation $S_{La}$ | Average particle size Ra (μm) | Standard deviation | Average particle size Rz (μm) | Standard deviation | | | |
| E61 | 0.02 | 16 | 1.45 | 0.58 | 0.58 | 0.40 | 1.32 | 0.56 | 98 | 0.53 | 916 |
| E62 | 0.3 | 15 | 1.51 | 0.68 | 0.60 | 0.41 | 1.55 | 0.61 | 98 | 0.70 | 886 |
| E63 | 0.5 | 15 | 1.63 | 0.72 | 0.71 | 0.53 | 1.83 | 0.84 | 98 | 0.81 | 675 |
| C61 | 0.6 | 15 | 1.72 | 1.82 | 1.73 | 0.53 | 2.11 | 1.01 | 98 | 1.01 | 478 |

The sixth embodiment detected a 3-point bending strength of each of the samples E61, E62, and E63, and the comparison sample C61 by the same method of the first embodiment. Table 6 shows the detection results according to the sixth embodiment.

As can be seen from the detection result shown in Table 6, the samples E61, E62, and E63 according to the present invention have the bending strength of not less than 500 MPa which is no problem in use.

On the other hand, the comparison sample C61 has the bending strength of less than 500 MPa, which is lower than that of each of the samples E61, E62, and E63 according to the present invention. It can be understood that containing the alumina grains having the particle size which exceeds 0.5 μm provides an insufficient function of suppressing growing of the zirconia grains, and thereby decreases the mechanical strength.

Accordingly, it is preferable for the solid electrolyte, to be used in gas sensors, to have the alumina grain having the particle size of not more than 0.5 μm. This can provide the solid electrolyte with a strong mechanical strength and a high thermal shock resistance.

It is more preferable for the alumina grains in the solid electrolyte to have the average value $A_{La}$ of not more than electrolyte 1 is the solid electrolyte produced by the first embodiment previously described.

The production of the gas sensor 4 according to the present invention firstly prepares the gas sensor element 5 having a structure shown in FIG. 8.

As shown in FIG. 8, the gas sensor element 5 has a structure in which a sensor substrate 6, a heater substrate 7, and a diffusion resistance layer 8 are stacked and then fired.

The sensor substrate 6 has the pair of the electrodes 61 and 62 formed on the surfaces of the solid electrolyte 1 (sample E1), to be applied to gas sensor elements, produced by the first embodiment.

The heater substrate 7 has a plurality of heaters 72 formed in a ceramic body 71 having an electric insulation function. The heaters 72 generate heat energy when receiving electric power. The diffusion resistance layer 8 is made of porous material through which an exhaust gas is passed. The exhaust gas to be detected is contacted with the target gas detection electrode 61. The diffusion resistance layer 8 is formed on one surface of the sensor substrate 6. The heater substrate 7 is formed on the other surface of the sensor substrate 6.

As shown in FIG. 8, the diffusion resistance layer 8 is formed on the surface of the solid electrolyte 1 having the target gas detection electrode 61. In this diffusion resistance layer 8, a spacer layer 82 and a porous diffusion resistance layer 83 are stacked in order to form a target gas chamber 81. A shield layer 84 is stacked on the other surface of the solid electrolyte 1, which is opposite to the surface on which the spacer layer 82 in the porous diffusion resistance layer 83 is formed. The porous diffusion resistance layer 83 is a sintered porous body made mainly of alumina. The spacer layer 82 and the shield layer 84 are made of sintered alumina composite with a high density. The pair of the electrodes 61 and 62 may be made of platinum (Pt).

The heater substrate 7 is formed on the surface, at the reference gas electrode 62 side, of the solid electrolyte 1. The heater substrate 7 is composed of the ceramic body 71 and the heaters 72. A wire pattern, which is made of platinum, is printed on the surface of each of the heaters 72. The ceramic body 71 is made of sintered alumina composite with a high density.

The gas sensor 4 according to the present invention incorporates the gas sensor element 5 therein. In the gas sensor 4, a first insulator 42 is placed in the inside of the housing case 41, and the first insulator 42 supports the gas sensor element 5.

The element cover 43 is fixed to a front end part of the housing case 41 so that the gas sensor element 5 is covered with the element cover 43.

A terminal part 59 placed at a rear end part of the gas sensor element 5 is covered with a second insulator 44. An atmosphere side cover 45 is fixed to the rear end part of the housing case 41. The second insulator 44 is covered with the atmosphere side cover 45.

In the structure of the gas sensor 4, the front end part indicates the part through which an exhaust gas pipe is inserted. The rear end part indicates the opposite part to the front end part in the gas sensor 4.

The element cover 43 is composed of an inside cover 431 and an outside cover 432. One or more gas-flow holes 433 are formed in the inside cover 431 and the outside cover 432. Through the gas-flow holes 433, the target exhaust gas is introduced into the inside of the gas sensor 4.

The gas sensor 4 is used in an exhaust gas pipe of an exhaust gas system so that the front end part of the gas sensor 4 is inserted in the inside of the exhaust gas pipe through which an exhaust gas emitted from an internal combustion engine flows. The housing case 41 of the gas sensor 4 is fixed to the exhaust gas pipe.

The solid electrolyte 1 which forms the gas sensor 4 according to the present invention is produced by the first embodiment previously described. That is, the solid electrolyte 1 has a high ion conductivity, and a high thermal shock resistance. Therefore even if stress such as a thermal shock is applied to the gas sensor element 5, it is possible to suppress generating of cracks in the solid electrolyte 1. This can suppress the low-temperature deterioration of the gas sensor 4 even if it is used at a low temperature. Accordingly, the gas sensor 4 can detect a concentration of $O_2$ gas and a concentration of NOx gas contained in an exhaust gas, and an A/F ratio of the exhaust gas with high accuracy. The presence or using of the solid electrolyte 1 can increase the reliability of the gas sensor 4.

While specific embodiments of the present invention have been described in detail, it will be appreciated by those skilled in the art that various modifications and alternatives to those details could be developed in light of the overall teachings of the disclosure. Accordingly, the particular arrangements disclosed are meant to be illustrative only and not limited to the scope of the present invention which is to be given the full breadth of the following claims and all equivalents thereof.

What is claimed is:

1. A solid electrolyte, for use in gas sensors, made of zirconia grains and fine alumina grains so that the fine alumina grains are dispersed in the grain boundaries of the zirconia grains using yttria as stabilizer, wherein
   the solid electrolyte contains a range of 2 to 10 mol % of yttria per zirconia grains, and a range of 10 to 15 mass % of alumina grains in the entire solid electrolyte, and
   the solid electrolyte has a relative density of not less than 93%,
   the zirconia grains after firing have an average particle size Rz of not more than 2 µm,
   the alumina grains after firing have an average particle size of not more than 1 µm,
   the average particle size of the alumina grains after firing is smaller than that of the zirconia grains after firing,
   an average distance value $A_{La}$ between the alumina grains after firing is not more than 2 µm,
   a standard deviation $S_{La}$ of the average distance value $A_{La}$ indicating a dispersion state of the alumina grains in a grain boundary of the zirconia grains in the solid electrolyte after firing is not more than 0.8,
   the solid electrolyte satisfies a relationship of $(S_{La}/A_{La}) \times Rz \leq 0.9$, and
   a sum of a grain boundary resistance and an internal grain resistance of the electrolyte having a size of 0.4 mm thickness and 16 mm diameter is within a range of 94.7 to 134.4 ohms at a temperature of 500° C., and the grain boundary resistance in a complex impedance of the solid electrolyte is within a range of 23.6 to 46.5 ohms.

2. The solid electrolyte according to claim 1, wherein the average particle size Ra of the alumina grains after firing is within a range of 0.4 to 0.6 µm.

3. The solid electrolyte according to claim 1, wherein the average distance value $A_{La}$ between the alumina grains after firing is not more than 1.5 µm, and a standard deviation $S_{La}$ of the average distance value $A_{La}$ is within a range of 0.5 to 0.6.

4. A gas sensor comprising:
   a gas sensor element;
   a housing case in which the gas sensor element is inserted and supported; and
   an element cover with which a front end part of the gas sensor element is covered, wherein the gas sensor element is comprised of the solid electrolyte according to claim 1 and a pair of electrodes in which a pair of the electrodes is formed on surfaces of the solid electrolyte.

5. A gas sensor comprising a solid electrolyte, the solid electrolyte including zirconia grains, fine alumina grains, and yttria, wherein the fine alumina grains are dispersed in the grain boundaries of the zirconia grains using yttria as a stabilizer,
   wherein the solid electrolyte contains a range of 2 to 10 mol % of yttria per zirconia grains, and a range of 5 to 25 mass % of alumina grains in the entire solid electrolyte, and
   the solid electrolyte has a relative density of not less than 93%,
   the zirconia grains after firing have an average particle size Rz of not more than 2 µm,
   the alumina grains after firing have an average particle size of not more than 1 µm,
   the average particle size of the alumina grains after firing is smaller than that of the zirconia grains after firing, an average distance value $A_{La}$ between the alumina grains after firing is not more than 2 μm, a standard deviation $S_{La}$ of the average distance value $A_{La}$ indicating a dispersion state of the alumina grains in a grain boundary of the zirconia grains in the solid electrolyte after firing is not more than 0.8, and the solid electrolyte satisfies a relationship of $(S_{La}/A_{La}) \times Rz \leq 0.9$, and wherein the solid electrolyte has a thermal expansion coefficient approximately equal to a thermal expansion coefficient of the alumina grains.

6. The gas sensor according to claim 5, wherein the average particle size Ra of the alumina grains after firing is within a range of 0.4 to 0.6 μm.

7. The gas sensor according to claim 5, wherein the average distance value $A_{La}$ between the alumina grains after firing is not more than 1.5 μm, and a standard deviation $S_{La}$ of the average distance value $A_{La}$ is within a range of 0.5 to 0.6.

8. The gas sensor according to claim 5, wherein the thermal expansion coefficient of the solid electrolyte is approximately within a range of $7.9 \times 10^{-6}$/° C. to $9.9 \times 10^{-6}$/° C.

\* \* \* \* \*